United States Patent
Bade et al.

(10) Patent No.: US 7,199,235 B2
(45) Date of Patent: Apr. 3, 2007

(54) PLANT PROMOTERS

(75) Inventors: Jacob Bernardus Bade, Leiden (NL); Jerome Hubertina Henricus Victor Custers, Alphen aan den Rijn (NL)

(73) Assignee: Syngenta Limited (GB)

( * ) Notice: Subject to any disclaimer, the term of this patent is extended or adjusted under 35 U.S.C. 154(b) by 0 days.

(21) Appl. No.: 10/478,603

(22) PCT Filed: May 31, 2002

(86) PCT No.: PCT/NL02/00354

§ 371 (c)(1),
(2), (4) Date: May 26, 2004

(87) PCT Pub. No.: WO02/097085

PCT Pub. Date: Dec. 5, 2002

(65) Prior Publication Data

US 2004/0237132 A1    Nov. 25, 2004

(30) Foreign Application Priority Data

May 31, 2001 (EP) ................... 01202055
Dec. 31, 2001 (EP) ................... 01205187

(51) Int. Cl.
*A01H 1/00* (2006.01)
*C07H 21/04* (2006.01)
*C12N 15/09* (2006.01)

(52) U.S. Cl. ................... 536/24.1; 435/6; 435/69.1; 435/71.1; 435/419; 435/320.1; 536/23.1; 800/278; 800/295

(58) Field of Classification Search ............... 536/23.1; 800/295; 435/320.1
See application file for complete search history.

(56) References Cited

U.S. PATENT DOCUMENTS 6,031,151 A * 2/2000 Draper ................. 800/298

OTHER PUBLICATIONS

Chao et al., Genomic sequence for *Arabidopsis thaliana* BAC T22C5 from chromosome I, complete sequence. Database accession No. AC012375 XP002187049. See sequence.*
Nakamura Y. *Arabidopsis thaliana* genomic DNA, chromosome 5, BAC clone:F15L12. Database accession No. AB026632 XP002237131. See sequence.*
Plant Cell Reports. 1994. vol. 14, pp. 125-130.*

* cited by examiner

*Primary Examiner*—Phuong T. Bui
(74) *Attorney, Agent, or Firm*—Michael E. Yates

(57) ABSTRACT

The present invention provides predominantly callus-specific promoters obtainable from *Brassica napus* plants. According to the present invention there is provided a DNA fragment harbouring a callus specific promoter, said DNA fragment being present in clone pJB1178-21 or clone pJB1178-43, respectively deposited with the Centraal Bureau of Schimmelcultures (Baarn, the Netherlands) on 6 Feb. 2001 under no. CBS 109271 and no. CBS 109273. The DNA fragment according to the present invention is further characterised in that it comprises the nucleotide sequence represented by SEQ ID NO: 1 or SEQ ID NO: 2 or the full length sequences as depicted in SEQ ID NO: 8 or SEQ ID NO: 9 respectively or parts thereof. Further, the invention comprises the homologue sequences in *Arabidopsis thaliana* as depicted in SEQ ID NO: 10 and SEQ ID NO: 11, respectively.

8 Claims, 7 Drawing Sheets

PLANT PROMOTERS

This application is a national stage application under 35 U.S.C. § 371 of International application No. PCT/NL02/00354, filed May 31, 2002, which is incorporated herein by reference and which is entitled to the benefit of European Patent Application Nos. 01202055.8 and 01205187.6, filed May 31, 2001 and Dec. 31, 2001, respectively, which are both incorporated herein by reference.

FIELD OF THE INVENTION

The present invention relates to new plant promoters and more specifically to callus specific promoters.

BACKGROUND

In the context of this disclosure, the term 'promoter' or 'promoter region' refers to a sequence of DNA, usually upstream (5') to the coding sequence of a structural gene, which controls the expression of the coding region by providing the recognition for RNA polymerase and/or other factors required for transcription to start at the correct site.

There are generally two types of promoters, inducible and constitutive promoters. An inducible promoter is a promoter that is capable of directly or indirectly activating transcription of one or more DNA sequences or genes in response to an inducer. In the absence of an inducer the DNA sequences or genes will not be transcribed. Typically, the protein factor, which binds specifically to an inducible promoter to activate transcription, is present in an inactivated form, which is then directly or indirectly converted to the active form by the inducer. The inducer can be a chemical agent; a physiological stress caused by environmental conditions, or can be an endogenously generated compound in response to changes in the development of the plant.

Constitutive promoters direct the expression of the DNA sequence (gene), which they control, throughout the various parts of the plants and continuously throughout plant development. However, the term 'constitutive' as used herein does not necessarily indicate that a gene is expressed at the same level in all cell types, but that the gene is expressed in a wide range of cell types, although some variation in abundance is often observed.

One of the earliest and most important inventions in the field of plant protein expression is the use of (plant) viral and *Agrobacterium*-derived promoters that provide a powerful and constitutive expression of heterologous genes in transgenic plants. Several of these promoters have been used very intensively in plant genetic research and are still the promoter of choice for rapid, simple and low-risk expression studies. The most famous are the 35S and 19S promoter from Cauliflower Mosaic Virus (CaMV), which was already found to be practical useful in 1984 (EP 0 131 623), and the promoters which can be found in the T-DNA of *Agrobacterium*, like the nopaline synthase (nos), mannopine synthase (mas) and octopine synthase (ocs) promoters (EP 0 122 791, EP 0 126 546, EP 0 145 338). A plant-derived promoter with similar characteristics is the ubiquitin promoter (EP 0 342 926).

A special group of the inducible promoters are the tissue- or development-specific promoters. These promoters have the property that they drive expression of the gene that they control predominantly in only one or a small group of tissues or predominantly during one developmental stage of the plant. Of course there also will be tissue-specific promoters that are developmental stage specific.

Promoters, which are predominantly functional in callus tissue, are relatively rare. A valuable application of such callus tissue specific promoters could be in the driving of selectable marker genes. During plant transformation selection of transgenics is predominantly done during tissue culture phase when callus is being formed and the callus differentiates into shoot and/or root tissue. Thus, expression of the selectable marker at this stage is required. Further, when the plants are developing into mature plants and in the mature stage itself, expression of the selectable marker serves no use anymore and it can even be considered as counterproductive. One example of this approach is demonstrated by Firek, S. et al. (1993, Plant Molecular Biology 22(1): 129–142), who used the callus-predominant *Asparagus* Aopr1-promoter to drive expression of the nptII gene. However, the number of this type of alternative promoters available from literature is limited.

It is therefore an aim of the present invention to provide a new plant-derived callus specific promoter.

It is a further aim of the present invention to provide fragments of DNA comprising the promoter according to the present invention.

It is a further aim of the present invention to provide transgenic plants (or parts and/or seeds thereof) comprising the promoter according to the present invention, including plants (or parts of plants) and seeds derived from said transgenic plants.

SUMMARY OF THE INVENTION

The present invention provides predominantly callus-specific promoters obtainable from *Brassica napus* plants.

According to the present invention there is provided a DNA fragment harbouring a callus specific promoter, said DNA fragment being present in clone pJB1178-21 or clone pJB1178-43, respectively deposited with the Centraal Bureau of Schimmelcultures (Baarn, the Netherlands) on 6 Feb. 2001 under no. CBS 109271 and no. CBS 109273.

The DNA fragment according to the present invention is further characterised in that it comprises the nucleotide sequence represented by nucleotide 1 to 678 of SEQ ID NO: 1 or nucleotide 1 to 644 of SEQ ID NO: 2

The DNA fragment according to the present invention is further characterised in that said fragment comprises the nucleotide sequence represented by SEQ ID NO: 8 or by the nucleotide sequence represented by SEQ ID NO: 9.

The invention further provides a DNA fragment capable of promoting predominantly callus tissue specific expression of an associated DNA sequence on reintroduction into a plant, characterised in that it comprises the nucleotide sequence represented by SEQ ID NO: 10 or parts thereof; or that it comprises the nucleotide sequence represented by SEQ ID NO: 11 or parts thereof.

Mores specifically the invention provides a DNA fragment capable of promoting predominantly callus tissue specific expression of an associated DNA sequence on reintroduction into a plant, characterised in that it comprises a nucleotide sequence as represented in SEQ ID NO: 8 starting at the nucleotide selected from the group consisting of: nucleotide 1, nucleotide 154, nucleotide 319, nucleotide 638, nucleotide 667, nucleotide 1402, nucleotide 1640, nucleotide 1802, nucleotide 1887, nucleotide 1919, nucleotide 1980, nucleotide 2203, nucleotide 2259, nucleotide 2407, nucleotide 2576, nucleotide 2598, nucleotide 2676, nucleotide 2871, nucleotide 2874 and nucleotide 3092; and ending at the nucleotide selected form the group consisting of nucleotide 154, nucleotide 319, nucleotide 638, nucleotide 667, nucleotide 1402, nucleotide 1640, nucleotide 1802, nucleotide 1887, nucleotide 1919, nucleotide 1980, nucleotide 2203, nucleotide 2259, nucleotide 2407, nucleotide 2576, nucleotide 2598, nucleotide 2676, nucleotide 2871, nucleotide 2874, nucleotide 3092 and nucleotide 3108.

In still another embodiment the invention provides a DNA fragment capable of promoting predominantly callus tissue specific expression of an associated DNA sequence on reintroduction into a plant, characterised in that it comprises a nucleotide sequence as represented in SEQ ID NO: 9 starting at the nucleotide selected from the group consisting of: nucleotide 1, nucleotide 1720, nucleotide 1889, nucleotide 1906, nucleotide 1991, nucleotide 2139, nucleotide 2375, nucleotide 2524, nucleotide 2585 and nucleotide 2634; and ending at the nucleotide selected form the group consisting of nucleotide 1720, nucleotide 1889, nucleotide 1906, nucleotide 1991, nucleotide 2139, nucleotide 2375, nucleotide 2524, nucleotide 2585, nucleotide 2634 and nucleotide 2650.

The present invention further includes a chimeric DNA sequence comprising, in the direction of transcription, at least one DNA fragment as herein before described and at least one DNA sequence to be expressed under the transcriptional control of said DNA fragment, wherein the DNA sequence to be expressed is not naturally under the transcriptional control of the DNA fragment. Preferably, the DNA sequence to be expressed codes for a selection marker.

The present invention further provides replicons comprising the abovementioned chimeric DNA sequences.

Also included in the present invention are microorganisms containing such a replicon, specifically pJB1178-21 and pJB1178-43, plant cells having incorporated into their genome, a chimeric DNA sequence as described above and plants essentially consisting of said cells. Such a plant may be a dicotyledonous plant or a monocotyledonous plant. Also parts of said plants selected from seeds, flowers, tubers, roots, leaves, fruits, pollen and wood, form part of the invention.

According to a further aspect of the present invention, there is provided use of a chimeric DNA sequence in the transformation of plants and use of a portion or variant of the DNA fragments according to the invention for making hybrid regulatory DNA sequences.

DESCRIPTION OF THE FIGURES

The present invention will now be described with reference to the following Figures which are by way of example.

DETAILED DESCRIPTION OF THE INVENTION

The present invention primarily concerns promoters or regulatory sequences naturally occurring in Brassica napus (oil seed rape). It has been found that genes under the regulatory control of these promoter or regulatory sequences are expressed predominantly in callus tissue of the plant.

Specifically the promoters of the invention are the promoters driving the gus::nptII gene in the constructs pJB1178-21 and pJB1178-43, respectively deposited with the Centraal Bureau of Schimmelcultures (Baarn, the Netherlands) on 6 Feb. 2001 under no. CBS 109271 and no. CBS 109273.

Figure 4:
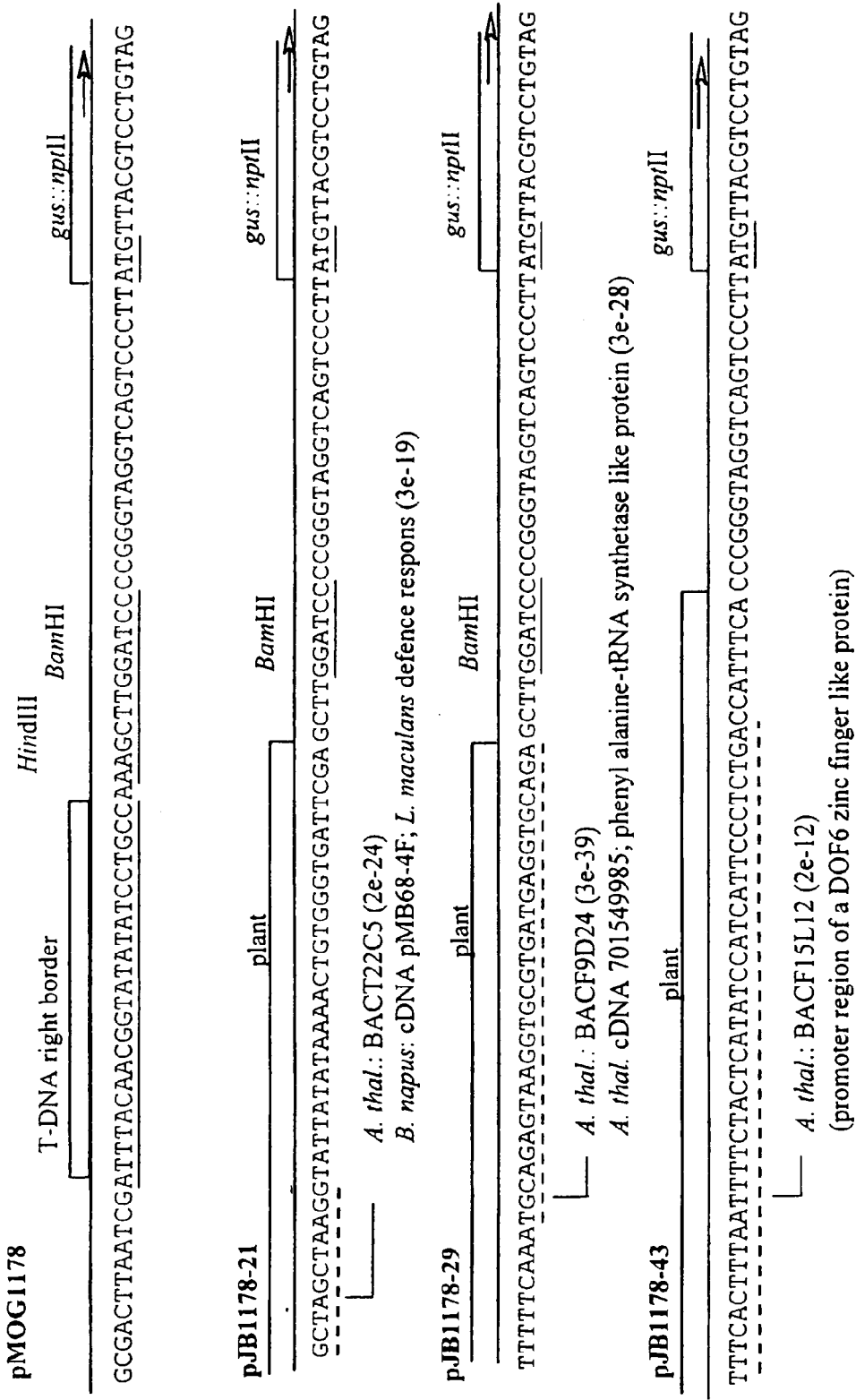
FIG. 4. Comparison of nucleotide sequences upstream of the gus::nptII coding region in tagging construct pMOG1178 and three transgenic lines (1178-21, 1178-29 and 1178-43). T-DNA right border, restriction sites (HindIII and BamHI) and start codon (ATG) of gus::nptII are underlined. Approximately 600 base pairs of sequence was determined for each line (single strand) and analysed via BLASTN searching. Homology was found with three BAC clones of Arabidopsis and cDNA clones of Arabidopsis and a B. napus. Start of homologous sequence is indicated (dashed line).

At first, approximately 600 base pairs of sequence was determined for each line (single strand) (nucleotides 1–678 of SEQ ID NO: 1 for pJB1178-21 and nucleotides 1–644 of SEQ ID NO: 2 for pJB1178-43) and analysed via BLASTN searching. This revealed significant homology for the sequence isolated from line 1178-21 with the *Arabidopsis* clone BACT22C5 ($2^{e-24}$) and the *Brassica napus* cDNA clone pMB68-4F ($3^{e-19}$). This cDNA is involved in defence response of *Brassica napus* after infection with the fungal pathogen *L. maculans*. The start of homologous sequence is indicated in FIG. 4. The sequence isolated from line 1178-43 has homology with *Arabidopsis* clone BACF15L12 ($2^{e-12}$), which has been indicated to be the promoter region of a predicted DOF6 zinc-finger like protein.

Further, the whole sequence of the promoters driving the gus::nptII gene in both constructs was sequenced (SEQ ID NO:8 and 9) and aligned with the corresponding *Arabidopsis* sequences (SEQ ID NO:10 and 11, respectively).

It is emphasized that the nucleotide sequence of the promoter of the invention may be subject to variations without significantly affecting the functionality, i.e. the specificity of the promoter. One of the possibilities to change the promoter is to delete certain fragments of the promoter while maintaining the elements that are necessary for the specificity. This can be accomplished by making several deletion mutants of the promoter, linking them up in a construct with a reporter gene (e.g. the gus gene or a gene coding for a fluorescent protein, like the GFP gene of *Aequoria*) and subsequently performing expression studies on plants transformed with said construct. Accordingly, also fragments of the promoter sequences of the constructs pJB1178-21 and pJB1178-43 driving predominantly callus specific expression, are part of this invention.

Furthermore, also promoter sequences formed by small changes in the nucleotide sequence by substitution or addition of nucleotides of the promoter sequences of the constructs pJB1178-21 and pJB1178-43 are included in this invention. It is envisaged that also in other species of plants homologous sequences can be found which have the same functionality as the sequences of the invention.

When comparing nucleic acid sequences for the purposes of determining the degree of homology or identity one can use programs such as BESTFIT and GAP (both from the Wisconsin Genetics Computer Group (GCG) software package) BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention when discussing homology of nucleic acid sequences, the comparison is made by alignment of the sequences along their whole length.

Preferably, sequences which have substantial homology have at least 50% sequence homology, desirably at least 70% sequence homology and more desirably at least 80%, 90% or at least 95% sequence homology, in increasing order of preference, with said sequences. In some cases the sequence homology may be 99% or above.

Desirably, the term "substantial identity" indicates that said sequence has a greater degree of identity with any of the sequences described herein than with prior art nucleic acid sequences.

The terms "regulatory sequence" or "regulatory region" and "promoter" are used interchangeably herein.

The present invention further provides chimeric DNA sequences comprising the DNA fragments of the present invention. The expression chimeric DNA sequence, as used herein, shall encompass any DNA sequence comprising DNA sequences not naturally found. For instance, chimeric DNA, as used herein, shall encompass DNA comprising the regulatory region, which is inducible in a non-natural location of the plant genome, notwithstanding the fact that said plant genome normally contains a copy of said regulatory region in its natural chromosomal location. Similarly, said regulatory region may be incorporated into a part of the plant genome where it is not naturally found, or in a replicon or vector where it is not naturally found, such as a bacterial plasmid or a viral vector. The term "chimeric DNA", as used herein, shall not be limited to DNA molecules which are replicable in a host, but shall also encompass DNA capable of being ligated into a replicon, for instance by virtue of specific adaptor sequences, physically linked to the regulatory region according to the invention. The regulatory region may or may not be linked to its natural downstream open reading frame.

The open reading frame of the gene whose expression is driven by the regulatory regions of the invention may be derived from a genomic library. In this situation, it may contain one or more introns separating the exons making up the open reading frame that encodes a protein according to the invention. The open reading frame may also be encoded by one uninterrupted exon, or by a cDNA to the mRNA encoding a protein according to the invention. Chimeric DNA sequences according to the invention also comprise those in which one or more introns have been artificially removed or added. Each of these variants is embraced by the present invention.

The promoters of the invention are especially useful for driving expression of a selection marker. Selection in transformation experiments is primarily done during tissue culture and the expression characteristics of the promoters of the invention, showing predominantly expression in callus tissue, are thus especially suited. Further, not only this specific expression in callus tissue, but also the less strong expression in other tissues is valuable when expressing a selection marker, since expression of the marker in stages and/or tissues which are not involved in selection of transformants is desirable.

In order to be capable of being expressed in a host cell, a regulatory region according to the invention will usually be provided with a transcriptional initiation region, which may be suitably derived from any gene capable of being expressed in the host cell of choice, as well as a translational initiation region for ribosome recognition and attachment. In eukaryotic cells, an expression cassette usually also comprises a transcriptional termination region located downstream of said open reading frame, allowing transcription to terminate and polyadenylation of the primary transcript to occur. Also, it is often the case that a signal sequence may be encoded, which is responsible for the targeting of the gene expression product to subcellular compartments. The principles governing the expression of a chimeric DNA construct, in a chosen host cell, are commonly understood by those of ordinary skill in the art. Furthermore, the construction of expressible chimeric DNA constructs is now routine for any sort of host cell, be it prokaryotic or eukaryotic.

In order for the chimeric DNA sequence to be maintained in a host cell, it will usually be provided in the form of a replicon comprising said chimeric DNA sequence (according to the invention) linked to DNA, which is recognised and replicated by the chosen host cell. Accordingly, the selection of the replicon is largely determined by the host cell of choice. Such principles as govern the selection of suitable replicons for a particular chosen host are well within the realm of the ordinary person skilled in the art.

A special type of replicon is one capable of transferring itself, or a part thereof, to another host cell, such as a plant cell, thereby co-transferring the open reading frame to the plant cell. Replicons with such capability are herein referred to as vectors. An example of such vector is a Ti-plasmid vector that, when present in a suitable host, such as *Agrobacterium tumefaciens*, is capable of transferring part of itself, the so-called T-region, to a plant cell. Different types of Ti-plasmid vectors (vide: EP 0 116 718 B1) are now routinely being used to transfer chimeric DNA sequences into plant cells, or protoplasts, from which new plants may be generated which stably incorporate said chimeric DNA in their genomes. Particularly preferred forms of Ti-plasmid vectors are the so-called binary vectors as claimed in (EP 0 120 516 B1 and U.S. Pat. No. 4,940,838). Other suitable vectors, which may be used to introduce DNA according to the invention into a plant host, nay be selected from the viral vectors, for example, non-integrative plant viral vectors, such as derivable from the double stranded plant viruses (for example, CaMV) and single stranded viruses, gemini viruses and the like. The use of such vectors may be advantageous, particularly when it is difficult to stably transform the plant host. Such may be the case with woody species, especially trees and vines.

The expression "host cells incorporating a chimeric DNA sequence according to the invention in their genome" shall encompass cells and multicellular organisms comprising or essentially consisting of such cells which stably incorporate said chimeric DNA into their genome thereby maintaining the chimeric DNA, and preferably transmitting a copy of such chimeric DNA to progeny cells, be it through mitosis or meiosis. According to a preferred embodiment of the invention, plants are provided which essentially consist of cells, which incorporate one or more copies of said chimeric DNA into their genome, and which are capable of transmitting a copy or copies to their progeny, preferably in a Mendelian fashion. By virtue of the transcription and translation of the chimeric DNA of the invention in some or all of the plant's cells, those cells that comprise said regulatory region will respond to wounding and thus produce the protein encoded by the open reading frame which is under control of the regulatory region. In specific embodiments of the invention, this protein will be an antipathogenic protein capable of conferring resistance to pathogen infections.

As is well known to those skilled in the art, regulatory regions of plant genes consist of distinct subregions with interesting properties in terms of gene expression. Examples of such subregions include enhancers and silencers of transcription. These elements may work in a general (constitutive) way, or in a tissue-specific manner. Deletions may be made in the regulatory DNA sequences according to the invention, and the subfragments may be tested for expression patterns of the associated DNA. Various subfragments so obtained, or even combinations thereof, may be useful in methods or applications involving the expression of heterologous DNA in plants. The use of DNA sequences according to the invention to identify functional subregions, especially the subregion conferring callus tissue specific expression, and the subsequent use thereof to promote or suppress gene expression in plants is also encompassed by the present invention.

Further more, it is generally believed that use of a transcriptional terminator region enhances the reliability as well as the efficiency of transcription in plant cells. Use of such a region is therefore preferred in the context of the present invention.

Although the application only contains examples in *Brassica* and potato, the application of the present invention is advantageously not limited to certain plant species. Any plant species may be transformed with chimeric DNA sequences according to the invention.

Although some of the embodiments of the invention may not be practicable at present, for example, because some plant species are as yet recalcitrant to genetic transformation, the practising of the invention in such plant species is merely a matter of time and not a matter of principle, because the amenability to genetic transformation as such is of no relevance to the underlying embodiment of the invention.

Transformation of plant species is now routine for an impressive number of plant species, including both the *Dicotyledoneae* as well as the *Monocotyledoneae*. In principle, any transformation method may be used to introduce chimeric DNA according to the invention into a suitable ancestor cell, as long as the cells are capable of being regenerated into whole plants. Methods may suitably be selected from the calcium/polyethylene glycol method for protoplasts (Krens, F. A. et al., Nature 296, 72–74, 1982; Negrutiu I. et al., Plant Mol. Biol. 8, 363–373, 1987), electroporation of protoplasts (Shillito R. D. et al., Bio/Technol. 3, 1099–1102, 1985), microinjection into plant material (Crossway A. et al., Mol. Gen. Genet. 202, 179–185, 1986), DNA (or RNA-coated) particle bombardment of various plant material (Klein T. M. et al., Nature 327, 70, 1987), infection with (non-integrative) viruses and the like. A preferred method according to the invention comprises *Agrobacterium*-mediated DNA transfer. Especially preferred is the use of the so-called binary vector technology as disclosed in EP A 120 516 and U.S. Pat. No. 4,940,838. A further preferred method for transformation is the floral dip method Is essentially as described by Clough and Bent (1998) Plant J. 16: 735–743.

Tomato transformation is preferably essentially as described by Van Roekel et al. (Plant Cell Rep. 12, 644–647, 1993). Potato transformation is preferably essentially as described by Hoekema et al. (Hoekema, A. et al., Bio/Technology 7, 273–278, 1989).

Generally, after transformation, plant cells or cell groupings are selected for the presence of one or more markers which are encoded by plant expressible genes co-transferred with the nucleic acid sequence encoding the protein according to the invention, after which the transformed material is regenerated into a whole plant.

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or electroporation (Shimamoto et al. Nature 338, 274–276, 1989). Transgenic maize plants have been obtained by introducing the *Streptomyces hygroscopicus* bar-gene, which encodes phosphinothricin acetyltransferase (an enzyme which inactivates the herbicide phosphinothricin), into embryogenic cells of a maize suspension culture by microprojectile bombardment (Gordon-Kamm, Plant Cell, 2, 603–618, 1990). The introduction of genetic material into aleurone protoplasts of other monocot crops such as wheat and barley has been reported (Lee, Plant Mol. Biol 13, 21–30, 1989). Wheat plants have been regenerated from embryogenic suspension culture by selecting only the aged compact and nodular embryogenic callus tissues for the establishment of the embryogenic suspension cultures (Vasil, Bio/Technol. 8, 429–434, 1990). The combination with transformation systems for these crops enables the application of the present invention to monocots.

Monocotyledonous plants, including commercially important crops, such as rice and corn are also amenable to DNA transfer by *Agrobacterium* strains (vide WO 94/00977; EP 0 159 418 B1; Gould J, et a., Plant. Physiol. 95, 426–434, 1991).

Following DNA transfer and regeneration, putatively transformed plants may be evaluated, for instance using Southern analysis to monitor the presence of the chimeric DNA according to the invention, copy number and/or genomic organization. Additionally or alternatively, expression levels of the newly introduced DNA may be undertaken, using Northern and/or Western analysis, techniques well known to persons having ordinary skill in the art.

Following such evaluations, the transformed plants may be grown directly, but usually they may be used as parental lines in the breeding of new varieties or in the creation of hybrids and the like.

To obtain transgenic plants capable of constitutively expressing more than one chimeric gene, a number of alternatives are available including the following:

A. The use of DNA, for example, a T-DNA on a binary plasmid, with a number of modified genes physically coupled to a selectable marker gene. The advantage of this method is that the chimeric genes are physically coupled and therefore migrate as a single Mendelian locus.

B. Cross-pollination of transgenic plants each already capable of expressing one or more chimeric genes, preferably coupled to a selectable marker gene, with pollen from a transgenic plant which contains one or more chimeric genes coupled to another selectable marker. The seed, obtained by this crossing, maybe selected on the basis of the presence of the two selectable markers, or on the basis of the presence of the chimeric genes themselves. The plants obtained from the selected seeds can then be used for further crossing. In principle, the chimeric genes are not on a single locus and the genes may therefore segregate as independent loci.

C. The use of a number of a plurality of chimeric DNA molecules, for example, plasmids, each having one or more chimeric genes and a selectable marker. If the frequency of co-transformation is high, then selection on the basis of only one marker is sufficient. In other cases, the selection on the basis of more than one marker is preferred.

D. Consecutive transformation of transgenic plants already containing a first, second etc., chimeric gene with new chimeric DNA, optionally comprising a selectable marker gene. As in method B, the chimeric genes are in principle not on a single locus and the chimeric genes may therefore segregate as independent loci.

E. Combinations of the above mentioned strategies.

The actual strategy may depend on several easily determined considerations, such as the purpose of the parental lines (direct growing, use in a breeding programme, use to produce hybrids). The actual strategy is not critical with respect to the described invention.

EXAMPLES

General

Plant Material

All transformation experiments described were performed with hypocotyl segments of *Brassica napus* variety 'Westar'. Tissue culture conditions were essentially as described by Bade and Damm (1995, In: Gene Transfer to Plants; Potrykus, I.; Spangenberg, G. Eds. Springer Verlag: Berlin; pp 32–38). For seed production or chromosomal DNA isolation transgenic plants were grown in pots (diameter 15 cm) in a greenhouse with the following conditions: 21–24° C., 60–80% humidity and a 16 hour light cycle. The potato material used for transformation experiments were in vitro stem explants from *Solanum tuberosum* variety 'Desiree'.

Bacterial Strains

*Escherichia coli* strain DH5α (Clonetech) and DH10B (Clonetech) were used for bacterial cloning. Strains were grown at 37° C. in LB medium supplemented with carbenicillin (100 mg/L), kanamycin (50 mg/L) or spectinomycin (50 mg/L) depending on the type of plasmid. *Agrobacterium tumefaciens* strain MOG301 (Hood et al., 1993, Transgenic Research 2:208–218), harbouring a non-oncogenic nopaline Ti-helper plasmid in a C58 chromosomal background, was grown at 29° C. in LB medium supplemented with kanamycin (100 mg/L) and rifampicin (20 mg/L).

Plasmid Constructions

Construct pMOG22 was described by Goddijn et al. (1993, Plant Journal 4(5):863–873). Vector pMOG448 was made in two steps. In the first step the HindIII 35S-gusintron fragment of p35SGUS.INT (Vancanneyt et al., 1990, Molecular and General Genetics 220:245–250) was cloned into pMOG22. Then the 5.8 kb XbaI fragment of pGH1 (Haughn et al., 1988, Molecular and General Genetics 211:266–271) was cloned in between the hpt and gus-intron parts. This particular fragment contains a mutant *Arabidopsis* acetolactate synthase gene (csr-1), which confers resistance to the herbicide chlorsulfuron. The coding region of the mutant als gene is still accompanied by its own 5' (2.5 kb) and 3' (1.3 kb) regulatory sequences.

Tagging constructs pMOG1178 and control pMOG964 contain plasmid rescue features (Koncz et al., 1989, Proceedings of the National Academy of Sciences of the United States of America 86:8467–8471.) but some modifications were made specifically for application in the *Brassica napus* transformation protocol. Due to the routine use of carbenicillin as antibiotic to control *Agrobacterium* it was decided to destroy the functionality of the amp gene and add a spectinomycin resistance gene instead. The constructs were made as follows.

The EcoR I site in pUC9 (Vieira and Messing, 1982, Gene 19:259–268) was modified by inserting an adapter made from oligo LS216 (5'AATTAGATCT 3')(SEQ ID NO: 3). The BglII site was then used for insertion of a 3 kb BamHI fragment containing a bacterial spectinomycin resistance gene isolated from plasmid Cel369 (unpublished, Leiden University). The amp resistance gene was disrupted by partial digestion with AvaII. Positive clones were selected for resistance to spectinomycin and susceptibility for carbenicillin.

A p35S-gus::nptII-tnos fusion gene (Datla et al., 1991, Gene 101:239–246) was isolated as HindIII-BglII fragment from pBI426 (Charest et al., 1993, Plant Cell Reports 12:189–193) and introduced in our spectinomycin vector, which was digested with HindIII and BamHI. This intermediate vector was linearised using HindIII, cloned in binary vector pMOG22 and named pMOG964.

The HindIII site of the above mentioned intermediate vector was changed into EcoRI using an adapter made out of primers SV5 (5'-AGCTCACGAATTCTCAGG-3') (SEQ ID NO: 4) and SV6 (5'-AGCTCCTGAGAATTCGTG-3')(SEQ ID NO: 5). The resulting vector was digested with BstBI and EcoRI and ligated into the likewise digested tagging vector pMOG553 (Goddijn et al., 1993; EMBL database accession number X84105). In this way a stretch of 1038 base pairs in pMOG553 was replaced by about 8 kb of new sequence without altering the right border configuration (gus-intron and octopine border). The new vector pMOG1178 appeared unstable in *E. coli* in the desired orientation. Hence the final cloning step was performed in *Agrobacterium*.

Constructs pJB1178-21, pJB1178-29 and pJB1178-43 were obtained via plasmid rescue (see below) from transgenic lines 1178-21, 29 and 43 respectively. These multicopy plasmids were linearised (EcoRI) and cloned as fragments in pMOG22 resulting in binary vectors pJBbin1178-21, pJBbin1178-29 and pJBbin1178-43 respectively.

Binary vectors were introduced in *Agrobacterium* strain MOG301 using electroporation (protocol Gibco BRL).

Plant Transformation

Hypocotyl segments were transformed according to the procedure described by Bade and Damm (1995, In: Gene Transfer to Plants; Potrykus, I.; Spangenberg, G. Eds. Springer Verlag: Berlin; pp 32–38;). Minor modifications were included as follows. Kinetin was omitted from the callus induction medium (CIM) and NAA (0.1 mg/L) was added to the regeneration medium (SIM). The concentration of kanamycin as selective agent was 15 mg/L. The sucrose level of the regeneration medium was lowered to 10 g/L to increase visual contrast between wildtype and transgenic callus. Shoot elongation was performed on non-selective medium (SEM). Transgenic nature of the plants produced was confirmed by rooting on hygromycin (5 mg/L) containing medium (SEM).

Potato in vitro stem explants were isolated one day prior to *Agrobacterium* inoculation. They were cultured in liquid callus induction medium (MS salts, B5 vitamines, sucrose 30 g/l, zeatin riboside 0.5 mg/l and 2,4-D 1.0 mg/l). After *Agrobacterium* inoculation (OD600 0.2, 20 minutes) the explants were cocultivated for 2 days on solidified callus induction medium (agar 8 g/l) and subsequently transferred to regeneration medium (MS salts, B5 vitamines, sucrose 30 g/l, cefotaxim 200 mg/l, vancomycin 100 mg/l and zeatin riboside 3.0 mg/l). About one week after transformation explants were transferred to fresh regeneration medium, which was supplemented with hygromycin (10 mg/l) or kanamycin (100 mg/l). This medium was refreshed biweekly. Shoots were harvested 8 weeks later and placed on selective rooting medium (½ concentrated MS salts, ½ concentrated B5 vitamines, sucrose 10 g/l, IBA 0.1 mg/l and hygromycin 5 mg/l).

gus Histochemical Assay

GUS activity in different plant parts of transgenic lines was investigated using histochemical analysis as described by Jefferson et al. (1987, Plant Molecular Biology Reporter 5:387–405). Samples of in vitro and in vivo plants were vacuum infiltrated for 5 minutes in a solution containing 5-Bromo-4-Chloro-3-Indolyl-β-D-glucuronicacid-cyclohexyl ammoniumsalt (0.5 mg/l); Na-P-Buffer (50 mM pH7); Na2-EDTA (5 mM pH 8.0); Triton X-100 (0.05% v/v); Potasium Ferrocyanyde (0.5 mM); Potasium Ferrocyanyde (0.5 mM). Samples were incubated for 3 hours at 37° C. and subsequently cleared from chlorophyll by washing with ethanol (70%). A classification of GUS activity (0–5=zero–very high) was made based on intensity of blue staining.

Callus Induction Assay

Small leaf disks (5*5 mm) of in vitro plants were placed adaxial side up on regeneration medium (SIM) supplemented with 2,4-D (1 mg/L). Sucrose level in the medium was kept at 10 g/L. After 3 weeks of culture new green callus was formed at the cutting edges and complete explants were histochemically stained for GUS activity.

Auxin Induction Assay

Node segments of in vitro plants were subculture on hormone free medium (SEM) supplemented with or without NAA (0.1 mg/L). After 3 weeks new leaves and roots were formed. At that time complete plants were histochemically stained for GUS activity.

PCR Analysis

Figure 1:
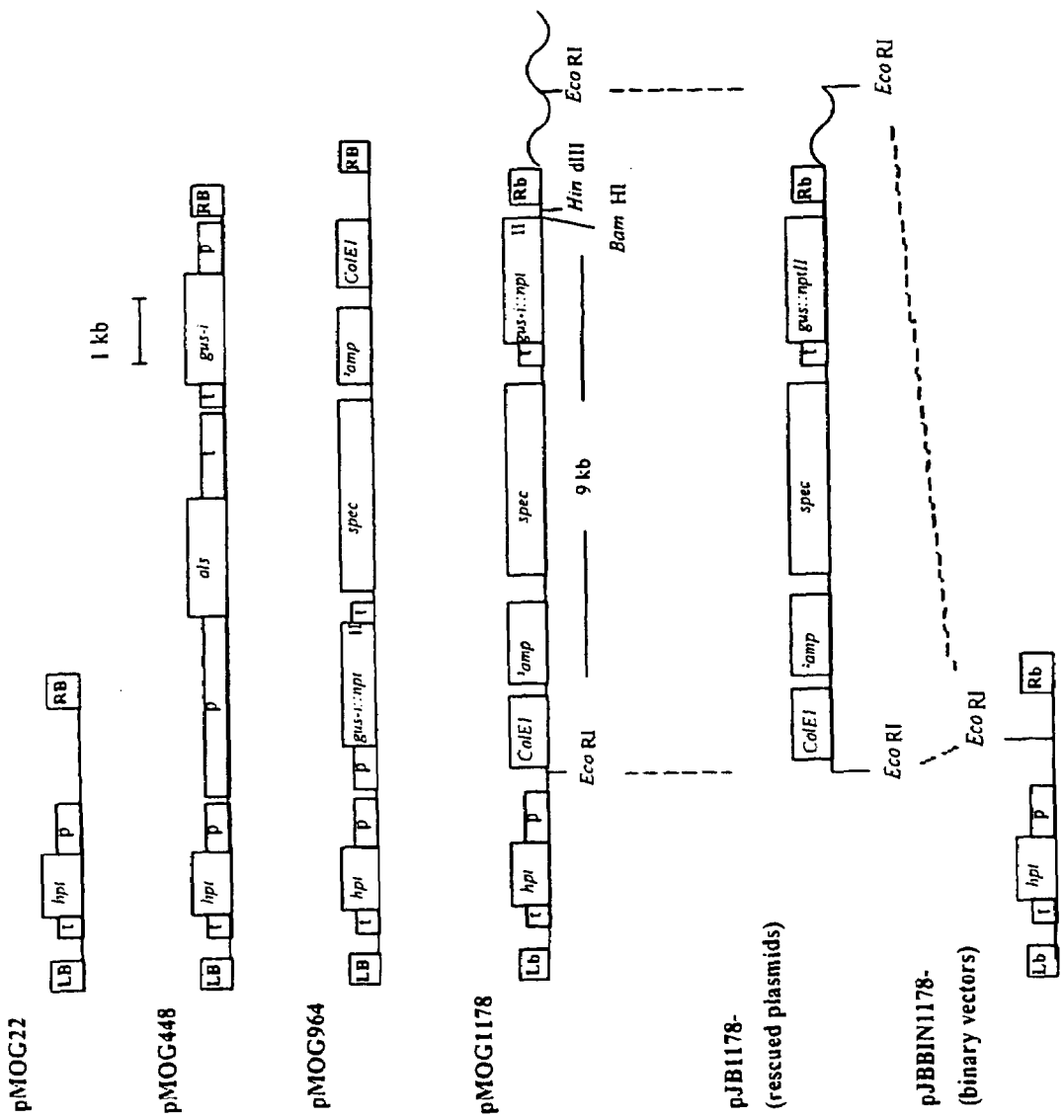
FIG. 1. Schematic overview of T-DNA structures in the constructs used for promoter tagging in Brassica napus. All binary vectors contain a 35S-hpt-nos cassette as in pMOG22 (Goddijn et al., 1993). Construct pMOG448 (chapter 3) was used as selection control (+hygromycin, −kanamycin). Construct pMOG964 contains a gus::nptII fusion gene (Datla et al., 1991) combined with a double enhanced 35S promoter, whereas tagging construct pMOG1178 has a promoterless version of the same coding region. The gus::nptII gene contains an intron in the gus part as described by Vancanneyt et al. (1990). Spectinomycin resistance and ColE1 origin of replication are included as plasmid rescue features. The ampicillin gene is disrupted (Δ) to avoid resistance of Agrobacterium to carbenicillin. Restriction sites used for the Southern blot analysis and plasmid rescue experiments are mapped (HindIII, EcoRI and BamHI). The waved line represents genomic plant DNA adjacent to the right border. LB left border, RB right border, p promoter, t transcriptional terminator sequence, hpt hygromycin phosphotransferase, als acetolactate synthase gene, gus-1 GUS reporter gene plus intron, nptII neomycin phosphotransferase gene spec 3 kb fragment including spectinomycin resistance gene, Δamp ampicillin resistance gene (non-functional), ColE1 ColE1 origin of replication.

Transgenic plants were analysed by PCR using the DNA sample preparation method as described by Thompson and Henry (1995). Small leaf pieces (±2 mm2) were taken from in vitro grown plantlets, sealed in micro-centrifuge tubes (1.5 mL) and frozen in liquid nitrogen. Twenty microliter extraction buffer (100 mM TrisHCL pH9.5; 1 M KCL; 10 mM EDTA) was added and samples were heated for 10 minutes at 95° C. After cooling down on ice samples were used directly or stored at 4° C. until use. PCR primers were: 5'-GTGACATCTCCACTGACGTAAG-3' (35S-P4) (SEQ ID NO: 6) and 5'-CGAACTGATCGTTAAAACTGCC-3' (SQ-GUS-192)(SEQ ID NO: 7). The primer annealing sites are indicated in FIG. 1. One PCR cycle of 5' 95° C., 5'° C., 5' 72° C. was followed by 30 cycles of 1' 95° C., 1' 55° C., 1' 72° C. A last cycle was carried out for 1' 95° C., 1' 55° C., 10'72° C. The reaction volume was 50 µl, containing 1 µl of DNA sample, Taq buffer, 1.5 mM MgCl2, 2*25 pmol primer, 200 µM dNTPs and 2.5 units Platinum Taq polymerase. PCR samples were analysed using electrophoresis in agarose gels.

Plasmid Rescue

Approximately 5 µg of EcoRI digested genomic DNA of individual transgenic lines was dissolved in 25 µl of H2O. Five µl T4 ligase (Gibco BRL), 60 µl T4 ligase buffer and 210 µl H2O were added and the mixture was incubated for 20 hours at 14° C. Ligated DNA was cleaned once using phenol-chloroform extraction (Sambrook et al. 1989, Molecular cloning: A laboratory manual, 2nd edition; Cold Spring Harbor Laboratory Press: Cold Spring Harbor, N.Y.) and subsequently dissolved in 10 µl TE. One µl of the solution was used for electroporation of one sample DH10B electromax (Gibco BRL) competent cells using a Cell porator system (Gibco BRL). Settings were used as suggested by the manufacturer. After one hour recovery in SOC medium, cells were spinned down, dissolved in 100 µl LB and plated on LB plates containing spectinomycin (50 mg/L). Colonies became visible after 24–48 hours incubation at 37° C. Subculture of individual colonies on plates and in liquid LB (Spec 50 mg/L) was used to confirm true resistant nature of the clones rescued.

Sequencing

Transition zones from the gus::nptII gene into the plant genome were sequenced using the AB1 sequencing kit (Prism BigDye Terminator Cycle) and 5'-CGAACT-GATCGTTAAAACTGCC-3' (SQ-GUS-192) (SEQ ID NO: 7) as single primer. Rescued plasmids or binary vectors were used as template DNA. Conditions were applied as suggested by the manufacturer. Approximately 500–600 bp of sequence was determined. Sequence data were analysed using BLASTN computer searching.

Example 1

Transformation of Brassica with Tagging Construct

Hypocotyl explants of Brassica napus were transformed with the tagging construct pMOG1178 (FIG. 1) and placed on medium containing 15 mg/L kanamycin which is the lowest concentration discriminating between resistant cell clusters and non-transgenic tissue. In the transformation experiments part of the explants was placed on hygromycin containing medium to select for expression of the 35S-hpt cassette. The frequency at which hygromycin resistant calli were obtained was used as a measure for the efficacy of T-DNA integration in a particular experiment. Construct pMOG448 (FIG. 1) was used as a negative control for kanamycin selection. The same construct and construct pMOG964 (FIG. 1) were used as positive controls for hygromycin selection. The latter construct was also used as the positive control for kanamycin selection.

From a series of 15 transformation experiments the results of three typical tagging experiments are presented in Table 1. The frequency at which hygromycin resistant calli were formed after transformation with pMOG1178 (number of resistant calli/explant* 100%) ranged from 55 to 99 percent. The callus frequency of the positive controls pMOG448 and pMOG964 ranged from 37 to 66 percent. After kanamycin selection, the callus frequency of the negative control pMOG448 was zero. The frequency obtained with the positive control pMOG964 was 81–119%. A low but significant number of kanamycin resistant calli (1.4–3.5%) were produced on explants transformed with the tagging construct pMOG1178.

The relative tagging frequency is the ratio between kanamycin and hygromycin resistant callus formation within a certain tagging experiment. This number represents the fraction of T-DNA inserts integrated behind a genomic promoter sequence that is active in callus tissue. The relative tagging frequency ranged from 2.6 to 3.8 percent between the different experiments.

This non-selective step was used to allow the development of tag lines with limited or no nptII expression after differentiation. Twenty out of the 36 regenerated plants showed normal root formation on hygromycin containing medium (5 mg/l), which indicated expression of the 35S-hpt cassette in roots. This observation confirmed the successful introduction of the promoterless gus::nptII tagging construct via kanamycin selection. Hygromycin-sensitive lines were excluded from further analysis.

Example 2

GUS Activity in Differentiated Plant Tissue

Kanamycin resistant control plants containing the 35S-gus::nptII construct (pMOG964) showed high levels of constitutive GUS activity (data not shown). Thus, the transgenic gus::nptII tag lines were expected to show GUS staining when the tagged genomic promoter was still active in certain plant tissues. Leaf, stem and root tissue of in vitro and greenhouse grown plants were histochemically assayed (Table 2). Fifteen of the 20 lines showed a detectable level of expression in one or more parts of the plant in either greenhouse or in vitro. The blue staining was usually very weak and was often restricted to the vascular tissue of leaves and stem. In general, expression under greenhouse conditions was lower compared to in vitro conditions.

Four lines (1178-1, 26, 29 and 45) showed moderate to high levels of GUS activity in leaf, stem and root. Only one line (1178-26) showed a high constitutive expression pattern also after transfer to soil. Enhanced expression was observed in some shoot (1178-2 and 30) or root meristems (1178-21, 29,33,43 and 45).

GUS Activity in Re-Induced Callus

As a control a set of analyses was carried out to investigate the GUS enzyme levels in re-induced callus. It was expected that most of the lines showed some level of GUS activity in this phase, because the original promoterless gus::nptII insertion resulted in kanamycin resistant callus. Leaf disks of all lines were placed on shoot induction medium supplemented with 2,4-D (1 mg/l), which resulted in formation of green non-regenerating callus at the edges of

TABLE 1

Transgenic callus formation in Brassica napus experiments with a promoterless gus::nptll tagging construct. Hygromycin and kanamycin callus frequencies are calculated as number of resistant calli/explant * 100%; relative tagging frequencies as kanamycin freq/hygromycin freq * 100%. Datapoints are based on transformation of at least 150 hypocotyl explnats. Kanamycin selection experiments after transformation with pMOG1178 were performed with at least 500 explants.

| | | Exp. I | | | Exp II | | | Exp III | | |
|---|---|---|---|---|---|---|---|---|---|---|
| Construct | Marker/reporter | Hyg | Kana | kan/hyg | Hyg | Kana | kan/hyg | Hyg | Kana | kan/hyg |
| pMOG448 | 35S-hpt/35S-gus | 37 | 0 | 0 | 66 | 0 | 0 | — | — | — |
| pMOG964 | 35S-hpt/35S-gus::nptll | 40 | 81 | 203 | 59 | 119 | 202 | — | — | — |
| pMOG1178 | 35S-hpt/-gus::nptll | 92 | 3.5 | 3.8 | 99 | 3.2 | 3.2 | 55 | 1.44 | 2.6 |

Figure 2:
FIG. 2. GUS patterns in plant parts of transgenic Brassica napus lines containing tagging construct pMOG1178. High GUS activity in callus induced on in vitro leaf segments or T1 hypocotyl explants (A+B: line 1178-21; C+D: line 1178-43)

Eighty-seven kanamycin resistant calli were obtained from all tagging experiments. In total 36 calli were successfully regenerated. This callus regeneration frequency (41%) is within the range obtained normally. Shoot primordia were isolated and subcultured on medium without kanamycin.

the explants. Eighteen of the 20 lines showed a detectable level of GUS activity after 14 days of culture on this 2,4-D containing medium. Expression was mainly localised in callus tissue newly formed on the edges of the explants (FIG. 2a+b). Relative upregulated expression in callus compared to the rest of the explant, was found for 12 lines (1178-2, 5, 10, 11, 18, 21, 22, 30, 37, 40, 43 and 45). No detectable enzyme levels were found in other plant tissues investigated (see below).

Upregulated expression in callus was also observed when T1 hypocotyl segments of tag lines were placed on regeneration medium (FIG. 2c+d).

26) contained at least part of the 35S promoter, presumably originating from the 35S-hpt cassette, upstream of the promoterless gus::nptII gene. This was confirmed by sequencing the amplified fragments (data not shown). These lines were excluded from further analysis.

Genomic DNA of the remaining lines was digested with EcoRI (FIG. 1) and used for Southern blotting analysis.

TABLE 2

Semi-quantitative analysis of GUS activity in *Brassica napus* tagged lines. Lines with relative upregulation are marked*

| Promoter tag line | In vitro | | | | | | In vivo | | | | | Comments |
|---|---|---|---|---|---|---|---|---|---|---|---|---|
| | leaf | stem | root | shoot meristem | 2,4-D callus | NAA leaf | leaf | stem | root | shoot meristem | root meristem | |
| 1178-1 | 3 | 3 | 2 | 3 | 3 | 3 | 1 | 1 | 0 | 1 | 0 | 35S |
| 1178-2 | 0 | 1 | 1 | 1 | 1* | 0 | 0 | 0 | 0 | 1* | 0 | |
| 1178-5 | 1 | 1 | 1 | 2 | 3* | 2* | 0 | 1 | 1 | 1 | 0 | |
| 1178-10 | 0 | 0 | 0 | 0 | 4* | 0 | 0 | 0 | 1 | 0 | 0 | |
| 1178-11 | 0 | 0 | 0 | 0 | 1* | 0 | 0 | 0 | 0 | 0 | 0 | |
| 1178-18 | 0 | 0 | 0 | 0 | 1* | 1* | 0 | 0 | 0 | 0 | 0 | |
| 1178-21 | 1 | 1 | 1 | 2 | 4* | 2* | 0 | 1 | 0 | 0 | 1* | Single copy |
| 1178-22 | 0 | 0 | 0 | 0 | 5* | 0 | 0 | 0 | 1 | 0 | 0 | |
| 1178-26 | 5 | 3 | 2 | 0 | 5 | 5 | 5 | 3 | 1 | 2 | 0 | 35S |
| 1178-29 | 4 | 3 | 4 | 3 | 4 | 4 | 2 | 2 | 1 | 1 | 3* | Single copy |
| 1178-30 | 0 | 0 | 0 | 0 | 2* | 0 | 0 | 0 | 0 | 1* | 0 | |
| 1178-32 | 1 | 1 | 0 | 1 | 1 | 0 | 0 | 1 | 0 | 1 | 0 | |
| 1178-33 | 1 | 1 | 0 | 1 | 2* | 2* | 1 | 1 | 0 | 0 | 2* | |
| 1178-34 | 0 | 0 | 0 | 0 | 0 | 0 | 0 | 0 | 0 | 0 | 0 | |
| 1178-37 | 1 | 1 | 0 | 2 | 2* | 1 | 0 | 1 | 0 | 1 | 0 | |
| 1178-38 | 2 | 0 | 0 | 1 | 2 | 2 | 1 | 0 | 0 | 0 | 0 | |
| 1178-40 | 0 | 0 | 0 | 0 | 4* | 0 | 0 | 0 | 0 | 0 | 0 | |
| 1178-42 | 0 | 0 | 0 | 0 | 0 | 0 | 0 | 0 | 0 | 0 | 0 | |
| 1178-43 | 1 | 3 | 2 | 0 | 4* | 2* | 0 | 1 | 1 | 0 | 2* | Single copy |
| 1178-45 | 2 | 2 | 1 | 1 | 5* | 4* | 1 | 1 | 1 | 1 | 2* | |
| # tg: 20 | 11 | 11 | 8 | 10 | 18 (13) | 11 (6) | 6 | 10 | 7 | 9 (2) | 5 (5) | |

GUS Activity Upregulated by Auxin Treatment

Since T-DNA integration is thought to occur in actively transcribed regions of the genome (Koncz et al., 1989, Proceedings of the National Academy of Sciences of the United States of America 86:8467–8471) and in this occasion integration of the promoterless gus::nptII tagging construct took place during culture on auxin containing medium (cocultivation with 2,4-D and selection with NAA), we wished to check upregulation of the tagged promoters by auxin. In vitro plant material of all tag lines was cloned. At least one node segment of each line was propagated on NAA (0.1 mg/l) containing medium. Plantlets grown on this medium developed significantly more and thicker roots, but were otherwise comparable to the control clones grown on hormone free medium. Histochemical GUS assays were performed 4 weeks after subculture. Six lines (1178-5, 18, 21, 33, 43 and 45) showed NAA induced GUS activity in the leaves.

An overview of the GUS expression data is presented in Table 2. In two transgenic lines (1178-34 and 1178-42) no GUS staining was observed.

Example 3

Isolation of Genomic 'Promoter' Sequences

Before the actual isolation of genomic sequences upstream of the tagging construct, all lines were screened by PCR to detect possible scrambled T-DNA insertions. Using a 35S-gus primer-set it was found that two lines (1178-1 and Single T-DNA insertions were detected in lines 1178-21, 29 and 43. The T-DNA right border fragments were approximately 12 kb in size (data not shown), which indicates ±3 kb genomic sequence between T-DNA and EcoRI restriction site. Results of the other lines were difficult to interpret due to the very large sizes of the EcoRI fragments.

Figure 3:
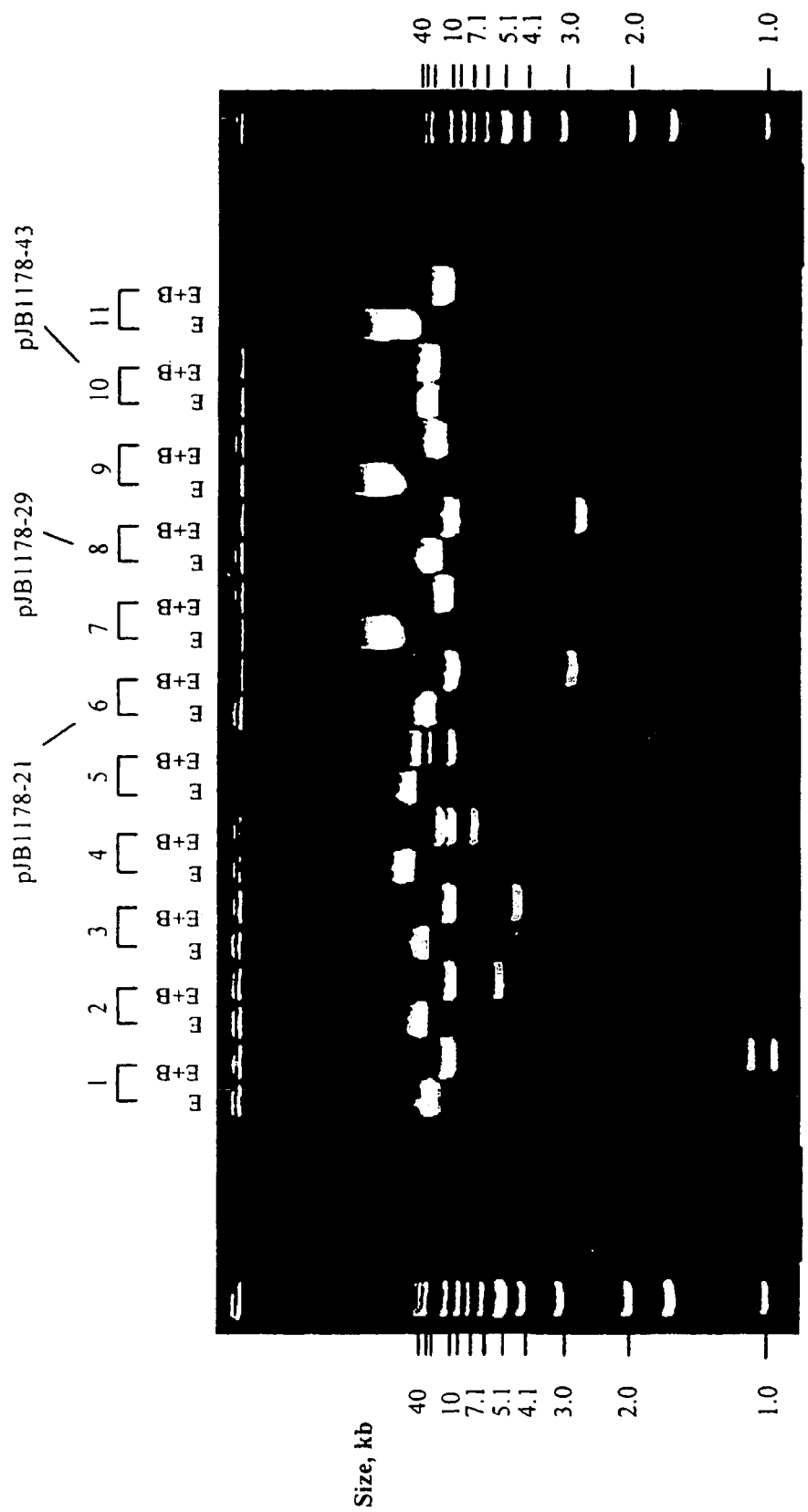
FIG. 3. Restriction analysis of rescued plasmids. Eleven different fragments of genomic sequence upstream of the gus::nptII tagging region were isolated via plasmid rescue (see FIG. 1). DNA was isolated from the bacterial cultures, digested with EcoRI or EcoRI+BamHI and separated over an agarose gel (sets 1–11). Positions of 1 kb markers (Gibco-BRL) are indicated. The genomic fragments isolated from the three single copy lines (1178-21, 1178-29 and 1178-43) were used for sequence analysis, construction of binary vectors and re-transformation to wildtype Brassica napus.

Digested DNA was also used for plasmid rescue experiments. Despite the large fragment sizes observed on the Southern blot, spectinomycin resistant colonies were readily obtained. Rescued plasmids were checked by restriction enzyme analyses. These analyses were done using EcoRI, expected to linearize the plasmids. A double digest with EcoRI plus BamHI was used to separate the original T-DNA (vector) of 9 kb from the newly isolated genomic sequences (FIG. 1). Plasmid rescue from the single copy T-DNA lines (1178-21, 29 and 43) resulted in identical clones within lines, whereas other lines showed 2 or more different restriction patterns (data not shown). It is likely that these different restriction patterns represented rescued fragments of different T-DNA insertions. Some examples of rescued plasmids digested with the enzyme combinations are shown in FIG. 3. The plasmids rescued from the single copy lines (1178-21, 1178-29 and 1178-43) are indicated and named according to the originating tag line (pJB1178-21(=pMOG2001), pJB1178-29(=pMOG2002) and pJB1178-43 (=pMOG2003)).

The linear fragments (EcoRI) range in size from ±11 kb (clone 1) to ±40 kb (clones 4 and 5). The fragment sizes (±12 kb) of the plasmids from single copy T-DNA lines (pJB1178-21, pJB1178-29 and pJB1178-43) match with the results obtained by Southern blotting (see above). In some cases (clones 7, 9 and 11) it appeared impossible to linearize the rescued plasmids by EcoRI digestion. Apparently the EcoRI site was destroyed. From the lanes with the double digestions, it can be seen that most of the clones show the expected 9 kb vector band (FIG. 3). Exceptions are those clones without the EcoRI site as mentioned above and pJB1178-43. All other clones contain, besides the 9 kb fragment, 1–3 other bands originating from the isolated plant DNA.

DNA sequences upstream of the gus::nptII gene were determined for each of the 3 single copy lines (1178-21, 1178-29 and 1178-43). The original right border and HindIII site of pMOG1178 (FIG. 1) were absent in all three lines (FIG. 4). In line 1178-43 the BamHI site (FIG. 1) was also not present anymore, which explains the absence of the expected 9 kb fragment after EcoRI*BamHI digestion (see above).

Analysis of Tagged Brassica Napus Promoter Sequences

The rescued Brassica napus promoter sequences of line 1178-21 (SEQ ID NO: 7) and line 1178-43 (SEQ ID NO: 8) were used in a BLAST (Altschul et al., Nucleic Acids Res. 1997; 25:3389–3402) search against the Arabidopsis genome sequence (TIGR: www.tigr.org/tdb/e2k1/ath1/). For both Brassica napus sequences extensive homology was found to a certain portion of the Arabidopsis genome. The 3078 bp Brassica sequence derived from tagging line 1178-21 displays high homology with a region on Arabidopsis chromosome 1 on BAC T22C5. The homology covers almost the entire region on Arabidopsis BAC T22C5 that represents predicted ORF T22C5.22 (unknown protein) with 9 exons. The homology with the Brassica sequence is the strongest in regions were predicted exons are located but the homology is also present, although more limited, in (predicted) intron regions. The Arabidopsis sequence homologous to the Brassica 1178-21 sequence is listed as SEQ ID NO:9. The sequence isolated from Brassica tagging line 1178-43 displays high homology to a region of Arabidopsis chromosome 5 located on BAC F15L12. In this region, between predicted ORF F15L12.8 (putative protein) and predicted ORF F15L12.10 (zinc finger protein like), the homology is found over the entire length of the isolated Brassica sequence. This region resembles the promoter region of ORF F15L12.10 on Arabidopsis chromosome 5. The Arabidopsis sequence homologous to Brassica napus promoter 1178-43 is listed under SEQ ID NO:10. Predicted gene F15L12.10 represents a zinc finger like protein with similarity to the Dof6 zinc finger like transcription factors.

The extensive homology found between the chromosomal regions of Arabidopsis thaliana ecotype Columbia and Brassica napus c.v. Westar shows the high level of genomic co-linearity between these closely related plant species.

Figure 6:
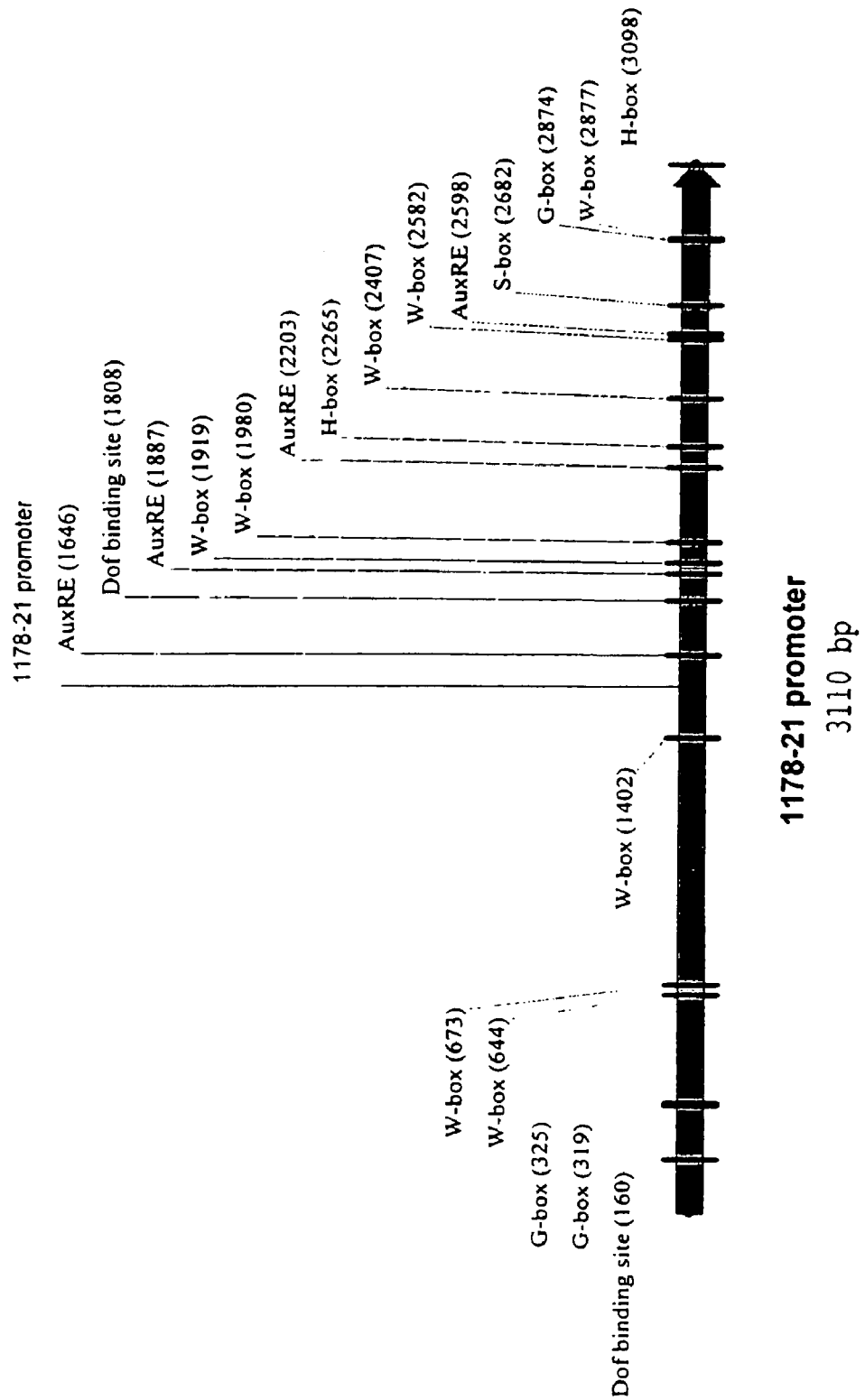
FIG. 6. Outline of the 1178-21 promoter and the sequence boxes containing promoter-elements. For explanation of the boxes, see example 7.
Figure 7:
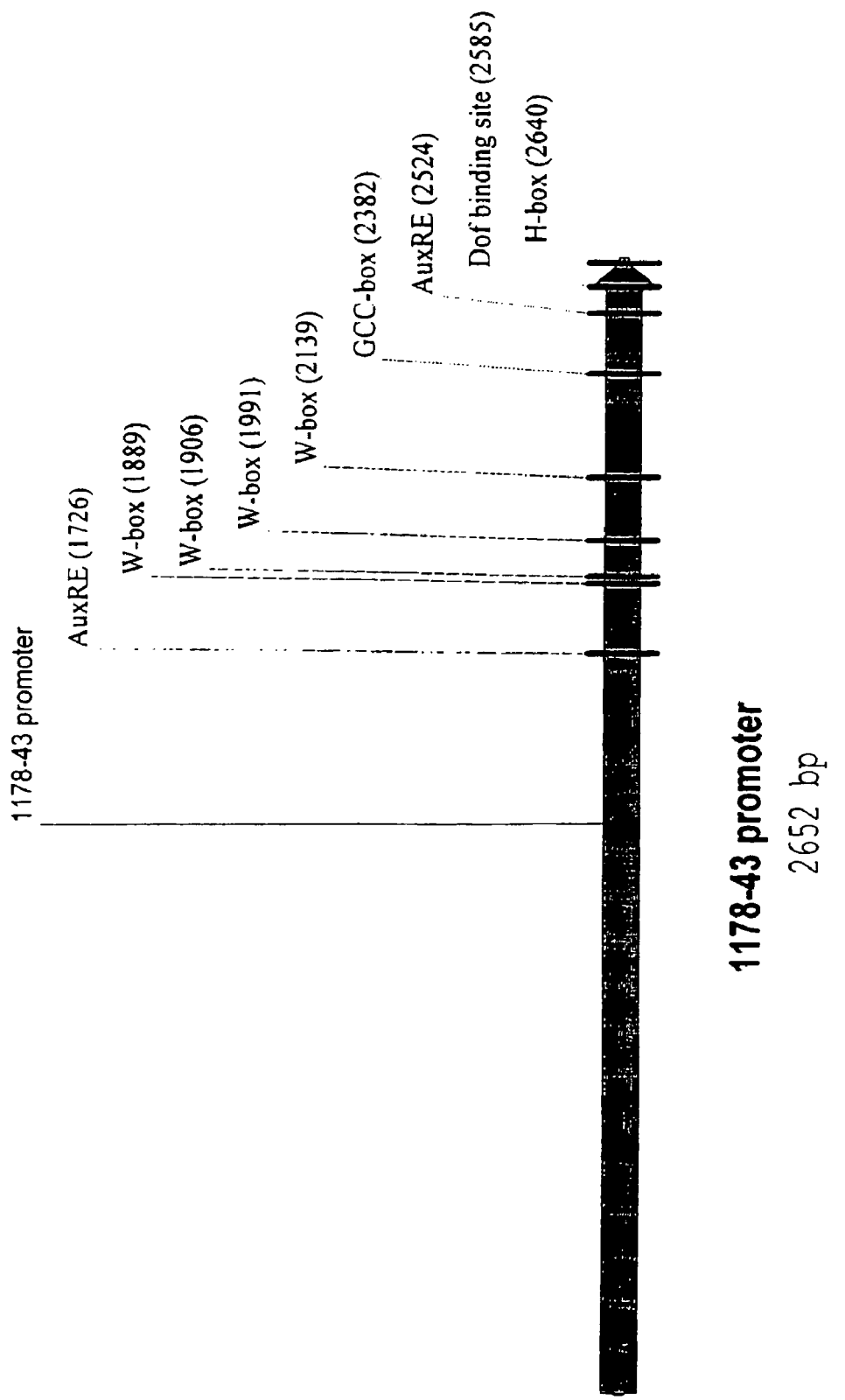
FIG. 7. Outline of the 1178-43 promoter and the sequence boxes containing promoter-elements. For explanation of the boxes, see example 7.

Both promoter sequences were analysed for the presence of promoter motifs known to play a regulatory role in auxin induced, pathogen induced (plant defence hormone responsive) and constitutive gene expression. Both promoters are very active in callus tissue and respond to auxin treatment. Next to this proven promoter activity there might be an involvement of pathogen and wound responsive elements in the regulation of gene expression driven by these two promoter sequences as they were identified in promoter trapping experiments during exposure to wounding and A. tumefaciens infection. Promoter elements identified in both promoters are indicated in FIG. 6 and 7. Elements were found containing the core sequence (TGTCTC) of the auxin responsive elements (AuxREs) required for auxin responsiveness of a soybean GH3 promoter (Ulmasov et al., Plant Cell 1995 October;7(10):1611–1623). Next to the presence of these auxin responsive elements sequences identical to a tobacco Dof protein NtBBF1 binding site found in the RolB oncogene promoter are present in both promoters. The NtBBF1 is probably the protein involved in mediating tissue specific and auxin inducible expression of RolB in plants (Baumann et al., Plant Cell 1999 March;11(3):323–334). Dof zinc finger proteins are also thought to be auxin inducible (Kang and Singh, Plant J. 2000; 21:329–339). Elements that occur in a high frequency in genes that are pathogen and/or stress inducible were also identified in both promoter sequences. The W-box motifs that are able to bind members of the plant WRKY family of transcription factors are present in both promoter sequences (8 and 4 copies respectively). The presence of a high frequency of W-box sequences (TTGACn) is associated with pathogen, elicitor and salicylic acid responsiveness (Eulgem et al., Trends Plant Sci. 2000;5(5):199–206). Sequences very similar to the H-box consensus (CCTAnC) as described by Lois et al. (EMBO J. 1989;8(6):1641–1648) and Fischer (Ph.D. thesis, University of Hohenheim, 1994) were found and these boxes are known to confer fungal elicitor and wound induced expression when fused as multimers to a plant minimal promoter (Takeda et al., Plant J. 1999;18(4):383–393). Also identified were boxes similar to the so-called G-box regulatory motif (CAmGTG, Loake et al., Proc. Natl. Acad. Sci. USA 1992; 89:9230–9234) and to the GCC-box (AGCCGCC) which is mainly found in the 5' upstream region of genes upregulated by the plant hormone ethylene (Ohme-Takagi and Shinshi, Plant Cell 1995 Feb; 77(2):173–182). The S-box is a very strong elicitor responsive element, which can confer very strong inducibility (WO 00/29592). The transcription start sites in both promoter fusions were not mapped and therefore it remains difficult to predict the location of a presumed TATA box in these promoters. Nevertheless there are sequences present that very well might function as a RNA polymerase II binding site.

Example 4

Evaluation of Isolated 'Promoter'-gus::nptII Plasmids

The three plasmids rescued from the single copy T-DNA lines (1178-21, 29 and 43) were selected for further analysis of promoter activity. Binary vectors were constructed by using a double selection strategy. Linear fragments (EcoRI) of the rescued plasmids were ligated with a linear fragment (EcoRI) of the binary vector pMOG22 (FIG. 1) and transformed to E. coli. Colonies were selected for kanamycin and spectinomycin resistance, indicating successful ligation. However, most of the binary clones appeared to contain a certain deletion, as evidenced by a reduction in size of the original 9 kb EcoRI/BamHI vector fragment (not shown). Sequence analysis of the promoter-gus fusions of the new binary vectors indicated unaltered presence of the genomic sequences directly upstream of the gus::nptII gene.

Figure 5:
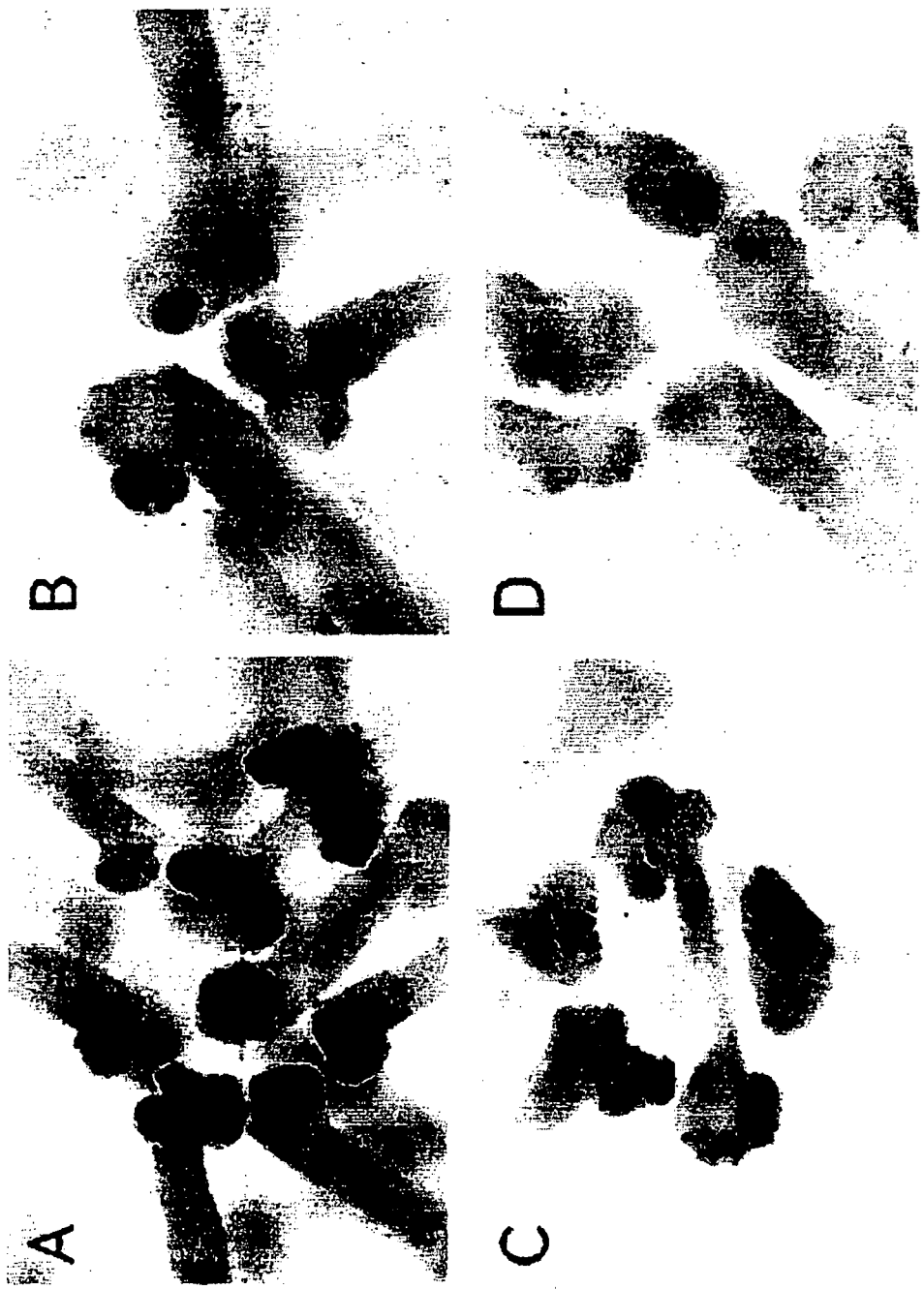
FIG. 5. GUS activity in young callus driven by new genomic sequences with promoter activity. Fragments upstream of the gus::nptII tagging gene (pMOG1178, FIG. 1) integrated in the genome of Brassica napus were isolated via plasmid rescue, cloned in binary vector pMOG22 (35S-hpt-nos, FIG. 1) and re-transformed to Brassica napus hypocotyl explants (Table 3). Histochemical XGluc staining (24 hours) was performed after 3 weeks of culture on hygromycin containing medium. A: very high expression of 35S-gus::nptII control construct pMOG964 (FIG. 1); B: good expression (pJBBIN1178-21); C: good expression (pJBBIN1178-29); D: moderate expression (pJBBIN1178-43).

Three to five binary vectors were selected per rescued plasmid. This selection was based on best resemblance with the expected restriction patterns using EcoRI and BamHI (data not shown). Twelve clones (4*pJBBIN1178-21, 5*pJBBIN1178-29 and 3*pJBBIN1178-43) were transferred to Agrobacterium strain MOG301 and subsequently transformed to Brassica napus. All transformations were carried out in duplo using ±100 hypocotyl explants each. Transformations with pMOG964 and pMOG1178 (FIG. 1) served as controls in these experiments. Five days after transformation about twenty explants per construct were evaluated for transient GUS activity. Five out of twelve clones showed GUS activity in hygromycin resistant callus. Three weeks after transformation hygromycin resistant calli were produced in all transformations, except for one 1178-43 binary clone. At this time point eight out of twelve clones showed GUS activity in hygromycin resistant callus (FIG. 5). Specifically clones from tag lines 1178-21 and 29 showed dark blue staining in the histochemical GUS assay.

Six binary vectors (2*pJBBIN1178-21, 2*pJBBIN1178-29 and 2*pJBBIN1178-43) were also used for potato transformation. Four of these showed transient GUS activity early after transformation. Five out of six vectors revealed stable GUS activity in developing hygromycin resistant calli. Approximately 50 potato explants per construct were used for a transformation experiment using kanamycin as selective agent. Putative transgenic shoots were harvested and tested for their true transgenic nature by placing them on hygromycin containing rooting medium. Only those shoots having an active35S-hpt cassette integrated in the genome would produce a normal root system. Five out of 6 constructs transformed produced one or more transgenic potato lines. The transformation frequencies (number of transgenic plants per explant*100%) ranged form 2 to 11 percent, which is comparable to the level obtained with the positive control construct pMOG964 (5%).

Preliminary results indicated that GUS activity in leaf samples of the transgenic potato lines varies from zero to relatively high. Some of the transgenic lines show only low GUS activity in leafs, but this level could be up-regulated when leaf explants were placed on callus induction medium (FIG. 5). An overview of the *Brassica* and potato transformation results is shown in Table 3.

TABLE 3

Transformation of *B. napus* and *S. tuberosum* with tagged promoter sequences

| | *B. napus* (hyg) | | *S. tuberosum* (hyg) | | *S. tuberosum* (kana) | | | | | | | |
| --- | --- | --- | --- | --- | --- | --- | --- | --- | --- | --- | --- | --- |
| Binary vectors | transient GUS | stable GUS | transient GUS | stable GUS | stable GUS | n | nr of reg expl | nr of shoots | nr hyg rooting | nr leaf GUS+ | nr callus GUS+ | transf freq % |
| pJBBIN1178-21-1 | +++ | +++ | +++ | +++ | +++ | 44 | 20 | 11 | 5 | 5 | 2 | 11 |
| pJBBIN1178-21-3 | − | − | | | | | | | | | | |
| pJBBIN1178-21-7 | − | − | | | | | | | | | | |
| pJBBIN1178-21-11 | + | ++ | ++ | + | ++ | 48 | 15 | 13 | 2 | 2 | 1 | 4 |
| pJB1178-29-1 | − | + | + | + | + | 46 | 3 | 7 | 5 | 4 | 2 | 11 |
| pJB1178-29-3 | +++ | +++ | | | | | | | | | | |
| pJB1178-29-4 | − | − | | | | | | | | | | |
| pJB1178-29-5 | − | + | | | | | | | | | | |
| pJB117B-29-11 | ++ | +++ | ++++ | ++ | ++++ | 54 | 7 | 7 | 1 | 1 | 0 | 2 |
| pJB1178-43-1 | − | + | − | − | + | 64 | 1 | 4 | 0 | − | − | 0 |
| pJB1178-43-2 | − | − | | | | | | | | | | |
| pJB1178-43-3 | + | ++ | − | + | ++ | 65 | 5 | 10 | 2 | 2 | 1 | 3 |
| pMOG964 | +++++ | +++++ | +++++ | +++++ | +++++ | 38 | 18 | 18 | 2 | 2 | 0 | 5 |
| pMOG1178 | − | − | − | − | − | 43 | 1 | 0 | 0 | − | − | 0 |

Table 3. Retransformation of *Brassica napus* and *Solanum tuberosum* with tagged promoter sequences. Transformation frequencies are calculated as number of transgenic lines per explant * 100%.

The invention claimed is:

1. An isolated DNA sequence having promoter function, wherein said sequence comprises SEQ ID NO:9 or a fragment thereof, and wherein said sequence promotes predominantly callus tissue specific expression of an associated DNA sequence on reintroduction into a plant.

2. The DNA sequence according to claim 1, wherein said DNA sequence consists of the nucleotide sequence represented by SEQ ID NO:9.

3. A chimeric DNA sequence comprising in the direction of transcription:
   (a) the sequence according to claim 1; and
   (b) a DNA sequence to be expressed under the transcriptional control of the sequence of (a), which DNA sequence is not naturally under the transcriptional control of the sequence of (a).

4. A replicon comprising the chimeric DNA sequence according to claim 3.

5. A micro-organism containing the replicon according to claim 4.

6. A plant cell comprising the chimeric DNA sequence according to claim 3.

7. A plant comprising the cell according to claim 6.

8. A part of a plant selected from the group consisting of seeds, flowers, tubers, roots, leaves, fruits, pollen and wood wherein said part contains the chimeric DNA sequence of claim 3.

* * * * *

SEQUENCE LISTING

```
<160> NUMBER OF SEQ ID NOS: 11

<210> SEQ ID NO 1
<211> LENGTH: 839
<212> TYPE: DNA
<213> ORGANISM: Brassica napus
<220> FEATURE:
<221> NAME/KEY: misc_feature
<222> LOCATION: (703)..(839)
<223> OTHER INFORMATION: gus::nptII sequence
<220> FEATURE:
<221> NAME/KEY: misc_feature
<222> LOCATION: (688)..(703)
<223> OTHER INFORMATION: BamHI restriction site

<400> SEQUENCE: 1 aagggaatt   acgccaccct   aaaaccttcc   taacaaaaag   ggtttggaaa   gggggaatta        60 atttttttgtc   ttgaacgcga   caaaaccggt   ggggttaatc   caagaattga   ttaccagggg      120 tttttcttc   ctcccaaaat   ttcctttat   aatttactat   tcaacaggag   cgtccaacat        180
taataatggg   tggtgggtcc   tcatccttc   ctgggtggtt   ttttaacaat   aaggcatgat        240
```

```
tttccccagt tgaactttt tgaagcattt cttgggggg gctttatcaa gcatatgcag    300
gtggttttct tatttgcaag ctttcccact ctcttagtct agggttttct ttctctagaa    360
gtggctgttt actgttactt cattcaattt tggcacaaca ggagaatgag ttccttcacg    420
atgtattcag cttcactcca agaaggttg gtggggaggt ttggcatgtc aagtgaagaa    480
aaggtttgtt ttgcgacttg catgctctcc tctttgttct ttgattgttt ccggttttaa    540
ccatcagttg gtgttcatta atggcagagg atgtttaaat caccaaactc agctctcaac    600
aaagcaagga cgcaattcct gaacaagcag aggatgctag ctaaggtatt atataaaact    660
gtgggtgatt cgagcttgga tccccgggta ggtcagtccc ttatgttacg tcctgtagaa    720
accccaaccc gtgaaatcaa aaactcgac ggcctgtggg cattcagtct ggatcgcgaa    780
aactgtggaa ttggtcagcg ttggtgggaa agcgcgttac aagaaagccg ggcaattgg     839

<210> SEQ ID NO 2
<211> LENGTH: 714
<212> TYPE: DNA
<213> ORGANISM: Brassica napus
<220> FEATURE:
<221> NAME/KEY: misc_feature
<222> LOCATION: (644)..(714)
<223> OTHER INFORMATION: gus::nptII sequence

<400> SEQUENCE: 2
tttccaattt aatcatctct tggtacactg aaaattgtat aaaaataaaa aaatccatat     60
ggaccaagag ttttattaaa tataattatg cggtttaaga aagggataat taaaaaaagc    120
ttaagaattt attattgact ttcctcaaat tttgaattat catctcttgt tatactgtac    180
acaagattta aaaaatggaa aaaccccctat aaaaatgaaa aatcatatga acagagttat    240
aagtataact tgtagtttaa gattttttt ttgtgtttag gtttacgcga acatttcag     300 tgagatccaa aacacttcaa tggacagtaa gatatgattt atgtatacat aatatataaa    360
tcataaacgg gcggctttat ggtctccaag tcacgttccg aattggttca cattattctt    420
tcatagcatt gtttaattta tcaataacag tattaataaa atctcagaat attatactcc    480
ataaaataaa taatatatga tcgaggccac gacaattgtg tctctctcat cccacattct    540
cgtgtatata tacatagctt ggcttttcct tctctttcac tttaattttc tactcatatc    600
catcattccc tctgaccatt tcacccgggt aggtcagtcc cttatgttac gtccgtgtag    660
aaaccccaac ccggaaatca aaaaactcga cggcctgtgg gcattcagtc tgga         714

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence:primer

<400> SEQUENCE: 3
aattagatct                                                            10

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 4
```
agctcacgaa ttctcagg                                          18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 5
agctcctgag aattcgtg                                          18

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 6
gtgacatctc cactgacgta ag                                     22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 7
cgaactgatc gttaaaactg cc                                     22

<210> SEQ ID NO 8
<211> LENGTH: 3110
<212> TYPE: DNA
<213> ORGANISM: Brassica napus
<220> FEATURE:
<221> NAME/KEY: protein_bind
<222> LOCATION: Complement((154)..(159))
<223> OTHER INFORMATION: Dof binding site
<220> FEATURE:
<221> NAME/KEY: misc_feature
<222> LOCATION: (319)..(324)
<223> OTHER INFORMATION: G-box
<220> FEATURE:
<221> NAME/KEY: misc_feature
<222> LOCATION: Complement((319)..(324))
<223> OTHER INFORMATION: G-box
<220> FEATURE:
<221> NAME/KEY: misc_feature
<222> LOCATION: Complement((638)..(643))
<223> OTHER INFORMATION: W-box
<220> FEATURE:
<221> NAME/KEY: misc_feature
<222> LOCATION: Complement((667)..(672))
<223> OTHER INFORMATION: W-box
<220> FEATURE:
<221> NAME/KEY: misc_feature
<222> LOCATION: (1402)..(1407)
<223> OTHER INFORMATION: W-box
<220> FEATURE:
<221> NAME/KEY: misc_feature
<222> LOCATION: Complement((1640)..(1645))
<223> OTHER INFORMATION: auxin-responsive element
<220> FEATURE:
<221> NAME/KEY: protein_bind
<222> LOCATION: Complement((1802)..(1807))
<223> OTHER INFORMATION: Dof binding site
<220> FEATURE:
<221> NAME/KEY: misc_feature
<222> LOCATION: (1887)..(1892)
<223> OTHER INFORMATION: auxin-responsive element

```
<220> FEATURE:
<221> NAME/KEY: misc_feature
<222> LOCATION: (1919)..(1924)
<223> OTHER INFORMATION: W-box
<220> FEATURE:
<221> NAME/KEY: misc_feature
<222> LOCATION: (1980)..(1985)
<223> OTHER INFORMATION: W-box
<220> FEATURE:
<221> NAME/KEY: misc_feature
<222> LOCATION: (2203)..(2208)
<223> OTHER INFORMATION: auxin-responsive element
<220> FEATURE:
<221> NAME/KEY: misc_feature
<222> LOCATION: Complement((2259)..(2264))
<223> OTHER INFORMATION: H-box
<220> FEATURE:
<221> NAME/KEY: misc_feature
<222> LOCATION: (2407)..(2412)
<223> OTHER INFORMATION: W-box
<220> FEATURE:
<221> NAME/KEY: misc_feature
<222> LOCATION: Complement((2576)..(2581))
<223> OTHER INFORMATION: W-box
<220> FEATURE:
<221> NAME/KEY: misc_feature
<222> LOCATION: (2598)..(2603)
<223> OTHER INFORMATION: auxin-responsive element
<220> FEATURE:
<221> NAME/KEY: misc_feature
<222> LOCATION: Complement((2676)..(2682))
<223> OTHER INFORMATION: S-box
<220> FEATURE:
<221> NAME/KEY: misc_feature
<222> LOCATION: Complement((2871)..(2876))
<223> OTHER INFORMATION: W-box
<220> FEATURE:
<221> NAME/KEY: misc_feature
<222> LOCATION: (2874)..(2879)
<223> OTHER INFORMATION: G-box
<220> FEATURE:
<221> NAME/KEY: misc_feature
<222> LOCATION: Complement((3092)..(3097))
<223> OTHER INFORMATION: H-box
<220> FEATURE:
<221> NAME/KEY: misc_feature
<222> LOCATION: (3108)..(3110)
<223> OTHER INFORMATION: translation start site

<400> SEQUENCE: 8
agtgttattc aatctcatag attatttata gactagattt aatttaagag tgtattttaa      60
tagatttggg gaaaattatg ttaaaaatat ataccactt aaattttata acttaaaact     120
gatactaact gataaacctt atatatttt ttataaagta attaaaatat ataagcaaaa     180
caagataccc gaaaactaaa acaagatcta ataaacatg ctacacgagg actataaatt     240
ataaaatgta ggtgtgtcca aaattaaatg aaatcatagt cacgtcggca tgagaggatc     300
caacggcata aaaagtgcca cgtgggagag catattccgt agatgtgaaa ggtttgattc     360
ttcttcgaaa tcaccgagtc gagagtcctc tacgcctctt ataaaaaact cgccgctctc     420
atcctcacgt ttctcttcct tcgttccttt ccttggcccc caaagtctga atctttctct     480
ctctctctcc ctgaaaagaa ccctctcttt aatggacata tcgcctctcc gatctcattc     540
ttcctccagg cttttgttgc tcttcttcta tagtattcgt gcttcgattc cctcttcttc     600
tgttgttgct tcccatcgta attgtcgtta gtccttttgt caaactcgga agcctctata     660
tcgattcgtc aatagttgat ttggatttga tataggaaac catggggagg agtaagcctc     720
tcttcttgat tttcaatctt tattgatttt aagtggttgg gaatgttgat ttcttgtgat     780
aaattgcaga gtctcagcgt aagaacgtcc ccatggattt gtttgatagt gatgatgata     840
```

-continued

```
caagtagtat tagctcctcc tccaccatgc gttctgagag acccggcatg gatgatgttc      900
aggttcacaa agatttgatg ctcgatcaat cccttgatgc tctctatgag aaaaggttgt      960
ttctttcgtt gtgggttttc ttgcttcatt ttgtttgaaa actgattttg tggattcctt     1020
tctggttgtg aaggacttcg actagagagc aagctttggc ctccattgtt gatgctttca     1080
acagcgactt gcagcatgag tttgtcgaaa agaagtaacc aactcgtttc ttgtttagtt     1140
tagcattcca ctttgagttc ctatgttgtt aatcatacta aggagtgtct aatgtttctt     1200
ctcaatgatg caggtttgcc acattattgc atcagtgctt acactgcacc aagaaagggt     1260
ccagcaagga gacctcttta gcatcacatg ttattggtta gtctttgagt aaaacaggca     1320
acttatgcat cattttcact agttttttt tttaattgag ctatactgac agttaatgtg      1380
gcgtttgcag ggttgctagc attgactgtt ggacttgggg atcaagcaca agagattctt     1440
gaagaatccg tcactcctct ttctcaggcc cttaaatctg gtcgtgaagt gttaaaaata     1500
acttcggtat ggatgagctg atgactagta gttttttatt ttgttaaagg tctggttcct     1560
aagtaaggcc atttcattgc agattcttga gtgtttggca gttataacct ttgttggtgg     1620
gaccaatccg gagcaaactg agacatctat gcaaataata tggcaaatga ttcaccccaa     1680
actaggttct aatgtatgca tcttactctt ttctcatgtt aaaccgagaa atctatgcaa     1740
attatttgct atttcattac tactactaat atggtttatt aagaaagtat gttgtttaat     1800
ctaaagtatg taggaggctc acatgtaagt tggcattttg tgtaggttgt tgcaaccaaa     1860
ccttcacctg ctgtgataac tactgttgtc tcttcctggg cgtttctgct cacaacagtt     1920
gaccgatgga ccctaagtcc caaactttgg caagagtaag tggaacttgt tgcatttatt     1980
tgacctagtg tcacttatta ctggatttat aatctcatta gagatattga tgctactgca     2040
ggatcgttac ttatctctcc tcactgttgg aaaaagatga ccgatctgta cgtatagctg     2100
ctggtgaagc gcttgctctg atatttgagt cgggaactct ggagaagttt gctgctgaag     2160
ccaaagagtc tgctaataat ggatcagtga agaaggaag cgtgtctcag gaggcattga     2220
ttcacatgca tggcctgaaa tccaaagtcg ttaaccaagt tagggacctc tctgtagagg     2280
caggtggtaa aggttctgct aagaaagatc tcaactcaca acggaatttg ttcaaagatc     2340
ttgttgaatt tcttgaggta tgagttcatc tttttctgtga tcttttgctc atgatgaggc     2400
taatctttga ctcttctggt tggattttta tatatatgat ttgttttaat taatgatgat     2460
taggatggat acgcacctga aacctctaca aaggttggag gggactattt gctgacgaca     2520
acgtggtatc agatgataca ggtttctctc aaatctttat attactatct acagacgtca     2580
acattatatg tgttgtttgt ctctatcttc ttgtgactgg tttttaacat atgcatgatt     2640
ttccacagtt gaacttttg aagcatttcc ttggggtgg ctttatcaag catatgcagg      2700
tcggttttct tatttgccaa gctttccact ctcttagtct taggttttct ttctctagaa     2760
gctggctgtt tactgttact tcattcaatt ttggcaacaa caggagaatg agttccttca     2820
cgatgtattc agcttcactc caaagaaggt tggtgggcga ggttctggca tgtcaagtga     2880
agaaaaggtt tgttttgcga ctctgcatgc tctcctcttt gttctttgat tgtttccggt     2940
tttaaccatc agttggtgtt cattaatggc agaggatgtt taaatcacca aactcagctc     3000
tcaacaaagc aaggacgcaa ttcctgaaca agcagaggat gctagctaag gtattatata     3060
aaactgtggg tgattcgagc ttggatcccc gggtaggtca gtcccttatg                 3110
```

<210> SEQ ID NO 9
<211> LENGTH: 2652

```
<212> TYPE: DNA
<213> ORGANISM: Brassica napus
<220> FEATURE:
<221> NAME/KEY: misc_feature
<222> LOCATION: Complement((1720))
<223> OTHER INFORMATION: auxin-responsive element
<220> FEATURE:
<221> NAME/KEY: misc_feature
<222> LOCATION: (1889)..(1894)
<223> OTHER INFORMATION: W-box
<220> FEATURE:
<221> NAME/KEY: misc_feature
<222> LOCATION: (1906)..(1911)
<223> OTHER INFORMATION: W-box
<220> FEATURE:
<221> NAME/KEY: misc_feature
<222> LOCATION: (1991)..(1996)
<223> OTHER INFORMATION: W-box
<220> FEATURE:
<221> NAME/KEY: misc_feature
<222> LOCATION: (2139)..(2144)
<223> OTHER INFORMATION: W-box
<220> FEATURE:
<221> NAME/KEY: misc_feature
<222> LOCATION: Complement((2375)..(2381))
<223> OTHER INFORMATION: GCC-box
<220> FEATURE:
<221> NAME/KEY: misc_feature
<222> LOCATION: (2524)..(2529)
<223> OTHER INFORMATION: auxin-responsive element
<220> FEATURE:
<221> NAME/KEY: protein_bind
<222> LOCATION: (2585)..(2590)
<223> OTHER INFORMATION: Dof-binding site
<220> FEATURE:
<221> NAME/KEY: misc_feature
<222> LOCATION: Complement((2634)..(2639))
<223> OTHER INFORMATION: H-box
<220> FEATURE:
<221> NAME/KEY: misc_feature
<222> LOCATION: (2650)..(2652)
<223> OTHER INFORMATION: translation start site

<400> SEQUENCE: 9
```

| | | | | | |
|---|---|---|---|---|---|
| tactgtgatt | cccccccccc | cccccccccc | cccccccaaa | aaaaacatct | gtctaatatt    60 |
| ttcatcacct | aatagcaaac | tctaatattt | ctttgttctg | tccaagtata | acagagttta   120 |
| tttaagacga | aattgagaat | tgtatgtata | tttttttatat | tgagattagt | agacaaaatt   180 |
| taaatttta | taaatttca | atgaaattat | acaagagttt | cacttcttaa | atgacctaaa   240 |
| acttatgcat | tttatatgtg | agaagaaaaa | ggtgaaaata | cgcctattag | aacatctcca   300 |
| atccgtactt | attttttctt | ctataaaaaa | agtggagatc | gacaaaaaaa | taaaatgtgc   360 |
| ctgaactgct | ggtgctataa | atttcttata | ctaattaaat | ttaaattcta | gtttaaataa   420 |
| ggtcatgatg | atcttgataa | aactgagagc | caaaggtatg | tagggtccaa | agagaaatat   480 |
| aatgattatc | tgttatattt | gtagaccaat | gattgtttgt | gaatgaataa | ccaatttcca   540 |
| tggcggaaaa | ctacaggtca | caacacatga | ttcttaccca | gtaccattc | tatcaaaaat   600 |
| aaaaccaaag | aaaaagtgta | ctaattaagt | gggatgtata | gaatagtgga | ttttaaaatt   660 |
| aaattaatag | tacctatta | aaaccagat | gtaacatgaa | tcaataccat | aaaatttaat   720 |
| aggttttgt | ttttttagta | aaacagcatg | ttttgtagta | ggccaacaaa | ataaatcact   780 |
| agagggcaac | cattttttat | taagagttta | gtcattctct | cttaacgttt | aaaaattggt   840 |
| gcgagttagt | agctcattt | ctcttcccac | gttacaacgt | ttaaaaatcg | tatatattgc   900 |
| acagcactat | atactaatct | gatgtatatg | gtccttagac | caaatctcgg | tcttcataga   960 |
| agtctctttc | ccgaaaaccg | atgtgtttga | gtgatttgct | ttaaatctcc | atgggataat  1020 |

| | |
|---|---|
| gcaaatacat catgagctgc acattctccg gctagttctt tgctttttta cttcatatat | 1080 |
| atttagatcc acgtacaaat ctaagaataa tatatgttac tagaagtatt ttattcacag | 1140 |
| ttatttaggt tagatttcga atatatcaac tatatataat aataaccata cgaagtatct | 1200 |
| taatatataa ttatggaata tgatgatata gctagttgtc ccactttcaa aaatcattgg | 1260 |
| ttgagtttca ttattgagta ctacgtacat ctgaatatga tttgtttgtt ttgtcgcaaa | 1320 |
| tacagtatgt ttccgcttgt ttcaattttt ttttaaataa aaaataaata tatagaatga | 1380 |
| cttcagtata tgtatttatg atgataagca aatatataat ttcagcatag atttttctgt | 1440 |
| gtataatcat ggtttgtttt gccaaaaatt aataagtata gtatatgaat tgttatttta | 1500 |
| tgtgtaaaat tcatatttgt atatgaattt attatttatg tgtaaaattc atatttctgt | 1560 |
| cagattgaat cagaataata caagggaaac tagagtatct gcccactccc tctagtacga | 1620 |
| tatgaaggtg atcactttga aaagatcgg tcccataagg aagaaacaag acatagcgat | 1680 |
| gagcatgggt ccctggtggt gacaactcaa cggaccattg agacataaaa tagaaattac | 1740 |
| aatacaaaga tgatgagtgt gcgtgggaat ccgacgtaga acatcatctt tcatcgatca | 1800 |
| tcgtacggtc attgttcatc ttaaatcaaa tagtaggatc gatttcacat tattgataac | 1860 |
| gattgcaact catcatcatc atatatattt gaccgctaaa ataatttgac caatccacta | 1920 |
| tcgtggagta acttaacgag aactcaaaac acaagttgaa gagataatta aaaagcgtaa | 1980 |
| gaatttatta ttgactttcc tcaaattaat tttcaattta tcatctcttg ttacactgta | 2040 |
| taattgtata aaaataaaaa aatcatatga acagagtttt ataaatataa ttatgcagtt | 2100 |
| taagaaagga taattaaaaa aagcttaaga atttattatt gactttcctc aaattttgaa | 2160 |
| ttatcatctc ttgttatact gtacacaaga tttaaaaaat ggaaaaacac cactataaaa | 2220 |
| atgaaaaatc atatgaacag agttataagt ataacttgta gtttaagatt ttttttttgt | 2280 |
| gtttaggttt acgcgaaaca tttcagtgag atccaaaaca cttcaatgga cagtaagata | 2340 |
| tgatttatgt atacataata tataaatcat aaacggcggc tttatggtct ccaagtcacg | 2400 |
| ttccgaattg gttcacatta ttctttcata gcattgttta atttatcaat aacagtatta | 2460 |
| ataaaatctc agaatattat actccataaa ataaataata tatgatcgag gccacgacaa | 2520 |
| ttgtgtctct ctcatcccac attctcgtgt atatatacat atgcttggct tttccttctc | 2580 |
| tttcactttta atttttctact catatccatc attccctctg accatttcac ccgggtaggt | 2640 |
| cagtccctta tg | 2652 |

<210> SEQ ID NO 10
<211> LENGTH: 3042
<212> TYPE: DNA
<213> ORGANISM: Arabidopsis thaliana

<400> SEQUENCE: 10

| | |
|---|---|
| atacatatgt tttataaatt ttatcatctt tttgaatgca tcataattta caatatttcg | 60 |
| attacgagaa aactagatga agagaacctt aaacatcctt tttaacataa aaaagaacac | 120 |
| taaactaaca caagttctac acattagtat aatttcttag ctgataaaaa acacaccatt | 180 |
| agtattttc cctttttggt aacgtttttt ttaagataat ctaaaccata atactgaatc | 240 |
| acaaagctca taaaaaagga aatcgaaatt ataatcacgt cggcaagtaa agagccaacg | 300 |
| gtgagggatg agccacgtgt gaaaggatat tccttagatg tgaatgggat ctaattcttg | 360 |
| tccgattaaa ccgagaagag tcttggtacg cctctctata tataaagtc atcactttcc | 420 |
| tcctcacgtt tcttcctttg gcatcgacga aagtctgaaa actctttct ctccacctct | 480 |

-continued

```
ttctctctta cccaaaacac aaaatctcct ctttaatgga tatatcgcct ctccgatctc      540
attcttcctc gttttatct gccaaactct tattgctctt cttcttttgt agttttcgtg       600
cttcttcgat ttcttcttct tcagttgttt cccatcgtcg taatccttct agctttcggt     660
ttctttgata attccctttg aattcgtttt tcttcttctt tcaatttccg caaataatca     720
gccgccgata agataatcat ggggaggagt aagatttctc ttcttcaatt tttattcttt    780
aattgattca atttgcaact ggatttgttt gttttagggt tttaattgat tactaattta    840
ctatgaaatc tcttatataa ccaatttctg ttttcgttaa cgcttttata aatttggatg   900
ctttgattaa cttttgctgg aattgttttt ttttgtgcag aatctcagcg taagaacgcg    960
acaatgtttg atagtgatga tgatacaagt agtgtaagct cttcctccac catgccatct   1020
gagagattgt tgaatcctgg tatggatgaa gttactgttc tcaaggatgc tttgttagat  1080
caatcccttg atgctctcta tgagaaaagg tttgtgtttc tttgttttct ttttgatgtg   1140
cttttgcttg attttgatgc aatactgata tttttggatt tgaaggagct caactagaga  1200
gcaagctttg gccaccattg ttgacgcatt taacagcgac ttgcagtatg agttgttga    1260 aaagaagtaa atatctgaca ctctttccta ttttagtttt atcaatccac gagtcttgtg  1320
tagtttaatc aatcatacat catacagaat ttaaccatgt ttcttcttaa tgagtgcagg  1380
tttgccactt tattgcacca gtgtttacac tgcaccaaga aagggtctac taaggagact  1440
tcattagcaa ctcatgtcat tggtgagtct cttagtaata gacaactcat gcatttttt    1500 ttgtcaagtc atattaacag ttaatcgtgg tggtttacag ggttgctagc gttaactgtt   1560
ggactcgggg atcatgcaca agaggttttg gaagaatctg tcactcctct gtctcaagcc  1620
cttaaatctg gtcgtgaaat cttgaaaata acttcggtat ggatgatttg ataatcgatc  1680
agtttgtcat tactttacag gtttcttaat aaggttcatc ttcgattcat ggttgttgat  1740
attctgcctt tcattgtag atacttgagt gtttagcagt cataaccttc gttggcggga   1800
atgatccaga gcaaaccgag aaatctatgc agattatctg gcaaatgatc cacccccaaac 1860 tagggtctaa tgtatgcatc ttactttttt ctcattttac aagccttttc aatctgattt  1920
attaagaaag taggctcaca tgaaggttgg cgttttttt gtaggttgtg gcaactaaac   1980
cttcacctgc tgtaataagt gctgttgtat cttcctgggc ttttctgctc acaacagttg  2040
atcggtggac tctaggtcct aaaattttc aagagtaagt ggggcatcat gcttttcttc  2100
gatctaattt tacttattca tagactgatt gaatattaat gtcattgcag gactgtaact  2160
tatctctcta cattgttgga aaaggatgac cgatctgtac gtatagctgc tggtgaagcg  2220
cttgcagtaa tatatgagtt gggaactcta gagaagttcg ctgccgaagt caaagggtct  2280
gctaatggat cagtgaaaga aggaggtgtc tctcaggaag cattgatgca catgcatggc  2340
ttgaaagcta aagtcactaa acaagttaga gagctctctg tagaggcagg tggtaaaggt  2400
tctgctaaga aagatctcaa cacccaacga aatttgttca aagatcttgt tgaatttctt  2460
gaggtatatc ttcttcacct tttctcctgt tgaggtttaa gttagactat tctgatagga  2520
ttttatatat gatgtgtttt aatgatgatt aggatggata tgctcctgaa acctcaacaa  2580
aagtcggagg ggactatttta cagacgtcaa cgtggtatca gatgatacag ttgaattatt  2640
tgaagcattt cctaggggggt ggcttttatta agcatatgca ggtctgtttt cttatttacc  2700
cttttctttc aagtgtcgaa ctctcttaag ttttctttgt tataaagctg acgctgtact   2760
gttttataca atttggttat caggagaatg aattccttca tgatgtattt agtttcactc  2820
```

-continued

```
caaagaagat tggtggagga aagttgtcta atgacgaaaa ggtatgtttc cggtatcttc      2880
attcactgtc tcgaatctta tcccattgca aaaaccttgt taacaaaact ggattttgcg      2940
attatttgtt gcagaggttg tttaaatcac caaactcagc tcttaacaaa gcaagaacgc      3000
agttcctggc caagcaaagg atgttagcta aggtattata aa                         3042
```

<210> SEQ ID NO 11
<211> LENGTH: 2246
<212> TYPE: DNA
<213> ORGANISM: Arabidopsis thaliana

<400> SEQUENCE: 11

```
atcatttaca taaattgaac ttaaaattta aagatggcca tcattattgg gataaaattt       60
gggagccaca agtaggtagg gtccaaaggg aaaatatcca tataatgatc atcatcagtt      120
atatttggag accaatgatt gtttgtgaat ggatcactaa attgttgtaa aaaagagaaa      180
gaacgaatga atcactattt tcctggcggg aattggtaat aacaaaatga tttttttttt      240
ttttccatcc tatcaaacat gaaacgaaag aaagagtata gtaagtggga tttattgaat      300
gattgatccg tctctagcta cttccattgt cacattaacg ttttcgtttt cgtagtaaac      360
aaagaaacat gttttcaact aagtagtaag acagaagaaa aaaattctag aggaacaagt      420
aacgatctta ttatgatata tactaacatg ggttactcat tttttttctc cacgacacaa      480
gatttaacat aaatcgtata ctatataaag attacgtaaa caataatata aaatatactg      540
tataatgttt tgtgtggata tggtccttag accaaatctc ggtctttcat agaagtctct      600
ttcccgaaaa ccaatgtggt agtgtgattt gtgtctctat gaactttaga tccccatcag      660
ataatgcgag cacatcatga gctacacatt gtccggcata ttctttgctt ttacttcatc      720
atgtgttcta tttacatata tacttatgat tatttataaa acaatgtaag cgtatattat      780
atccacaatt ttttaattta gatttcagag tagaattgta gttttattca acaaattata      840
taaagtataa tagagtataa atttagaatg aacaaaaaat tgtagcccaa tatgtcttga      900
caaaaataga aacatttgtg gtcctatcaa ataaagagtg ttggtccaag atgatttttt      960 tttcttttttg acagcaatga cattatattt gcttgatttt gaaatatatg tgtttaaaat     1020
taaggcaatg ggaatatgga ggacaaattt aaaatctctt tggtaaaatt ttcgataaaa     1080
gaaacaagac attatcgaat attttttatg cgctttacaa ttcacataat cctatcaaat     1140
cacataaaga aaccaactcg acaaatacaa attttagtat taaacacttt gattttgctt     1200
taaacatcga attagaatgt actcatatat gactgatcga aatagaaaat cacatatatt     1260
tgttcaatcc tctagagtac gaaggaacgg tacgttaggg tccacaagga agaacaagac     1320
attgcgatga gtatgggacc ctggtggtga caactcaacg gaccattgag acagcaacac     1380
agaaatgaca aagaagttga gtgcgtggga atccgacgtc gaacattatc tctcatccat     1440
catcgtacgg ttactattca tcttaatcaa atagatccga tttcacatta ttgataacga     1500
ttgcaagttt gcaactcaac attttttttat ttttttttat cgcttgaaga aattgaccga     1560
tacattattg tggaatgtgg agtgacgaag caagcttagt acatattata tcagactata     1620
gttatagatt ttaagctaca aaggttttat atagatctca agtttttgat gtggttatag     1680
gtttatagct ttactcataa cactacaatt gagtagtaag tttagttgtt tttatgagat     1740
tatatagtaa aaagatttgg taaatgttat ataaaaaaaa ttatgagaat taatttacac     1800
tagaaaatat attttaaaac ttacttcatt ttcaattttt agatatcaaa tcatacaaaa     1860
tgttgtttta tgaaactaat taatatataa ccttgtttga agtagcaatt tttaacaagt     1920
```

```
cttcaaacat taatatatga agagataata acattattag gttatactaa tttccacagg    1980
ctatcaaatg tagatttttt gttcgcatta taaattttt aataaacggc ggctttatgt    2040
ctgttccaag tcacgttccg aattggttca cattattctt cttagcattg tttgaaatat    2100
taaactaata atatgagatc gaggccacaa caacaattgt gtgtctctct cctcccacat    2160
tcccatccca tgtatatata cagatgcttg gcttttcctt ttgcttcact tttaatttct    2220
actcatatcc atcattctct ctgatc                                         2246
```